(12) United States Patent
Wu et al.

(10) Patent No.: US 9,393,316 B2
(45) Date of Patent: Jul. 19, 2016

(54) CANCER TARGETING PEPTIDES FOR ENHANCING ANTI-CANCER DRUG DELIVERY AND THERAPEUTIC EFFICIENCIES

(71) Applicant: Acedemia Sinica, Taipei (TW)

(72) Inventors: Han-Chung Wu, Taipei (TW); Chien-Hsun Wu, Taichung (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 14/499,201

(22) Filed: Sep. 28, 2014

(65) Prior Publication Data
US 2015/0202315 A1 Jul. 23, 2015

Related U.S. Application Data

(60) Provisional application No. 61/928,756, filed on Jan. 17, 2014.

(51) Int. Cl.
| | |
|---|---|
| *A61K 31/437* | (2006.01) |
| *A61K 31/704* | (2006.01) |
| *A61K 47/48* | (2006.01) |
| *C07K 7/08* | (2006.01) |

(52) U.S. Cl.
CPC ......... *A61K 47/48246* (2013.01); *A61K 31/437* (2013.01); *A61K 31/704* (2013.01); *A61K 47/48215* (2013.01); *A61K 47/48238* (2013.01); *A61K 47/48815* (2013.01); *C07K 7/08* (2013.01)

(58) Field of Classification Search
None
See application file for complete search history.

(56) References Cited

U.S. PATENT DOCUMENTS 7,399,644 B2 * 7/2008 Honma ................... C07K 7/06
435/176

FOREIGN PATENT DOCUMENTS

EP 1 371 983 A1 12/2003

OTHER PUBLICATIONS

Perche et al., Journal of Drug Delivery, 2013, article ID 705265, pp. 1-32.*
Perche et al., J. of Drug Delivery, 2013, ID 705265, 1-32.*
Hsiung et al (2008). Detection of colonic dysplasia in vivo using a targeted heptapeptide and confocal microendoscopy. Natural Medicine, 14(4), 454-456.
Kimberly A. Kelly and David A. Jones (2003). Isolation of a Colon Tumor Specific Binding Peptide Using Phage Display Selection. Neoplasia, 5(5), 437-444.
Rasmusssen et al. (2002). Tumor cell-targeting by phage-displayed peptides. Cancer Gene Therapy, 9, 606-612.

* cited by examiner

*Primary Examiner* — James H Alstrum Acevedo
*Assistant Examiner* — Roy Teller
(74) *Attorney, Agent, or Firm* — Hsiu-Ming Saunders; Intellectual Property Connections, Inc.

(57) ABSTRACT

A peptide targeted conjugate is disclosed. The conjugate comprises: (a) an isolated or a synthetic targeting peptide of less than 15 amino acid residues in length, comprising an amino acid sequence having at least 90% identity to a sequence selected from the group consisting of SEQ ID NOs: 1, 2 and 3; and (b) a component, to which the targeting peptide is conjugated, the component being selected from the group consisting of a drug delivery vehicle, an anti-cancer drug, a micelle, a nanoparticle, liposomes, a polymer, a lipid, an oligonucleotide, a peptide, a polypeptide, a protein, a cell, an imaging agent, and a labeling agent. The conjugate may further comprise an anti-cancer agent encapsulated within the drug delivery vehicle. Compositions and methods of treating cancer are also disclosed.

17 Claims, 8 Drawing Sheets

FIG. 8

Table 1. Alignment of phage-displayed peptide sequences selected by HCT116

| Phage clone | Phage-displayed peptide sequence | Binding activity |
|---|---|---|
| HCT-74 | S S M D I V L R A P L M | * * * |
| HCT-01 | A A P E L V A P S I W L | * * |
| HCT-40 | S L S L V A P V L S L L | * |
| HCT-70 | T M G F T A P R F P H Y | * |
| HCT-50 | S P G L S L V S H M Q T | * * * |
| HCT-41 | L T R P N G I P H L S L | * * * |
| HCT-21 | T S Y S I N L L S T P M | * * |
| HCT-10 | S P T G L F M T L S S R | * * * |
| HCT-04 | H H R T L S P S V S I L | * * |
| HCT-69 | T S V S I V S T V L T P | * * * |
| HCT-63 | R L N L D I I A V T S V | * * * |
| HCT-08 | L A T P F T A T S A T G | * * |
| HCT-71 | V T S S L P R M F H T L | * |
| HCT-12 | G F L P L P R G E I F S | * |
| HCT-92 | T P S L P P T M F R L T | * * |
| HCT-59 | G H L I P L R Q P S H Q | * |
| HCT-47 | S P N F S W L P L G T T | * |
| HCT-33 | K V D A G L G S I F L L | * * |
| HCT-34 | W G I T V E T A Y G T A | * * * |
| HCT-35 | S E L H V R L S H I N A | * * |
| HCT-45 | S S G G V R W S A H W S | * * |

AVFPMILW: Small (small + hydrophobic [includes aromatic - Y])
DE: Acidic
RK: Basic
STYHCNGQ: Hydroxy + Amine + Basic + Q

CANCER TARGETING PEPTIDES FOR ENHANCING ANTI-CANCER DRUG DELIVERY AND THERAPEUTIC EFFICIENCIES

REFERENCES TO RELATED APPLICATION

The present application claims priority to U.S. Provisional Application Ser. No. 61/928,756, filed Jan. 17, 2014, which is herein incorporated by reference in its entirety.

FIELD OF THE INVENTION

The present invention relates generally to cancer targeting peptides, and more specifically to peptide-targeted conjugates specific for cancer cells.

BACKGROUND OF THE INVENTION

Ligand-targeted nanoparticles encapsulated with chemotherapeutic agents play an increasingly important role in the treatment of cancer, and are expected to become the next generation of therapeutic modality. Colorectal cancer is one of the most commonly diagnosed cancers and a leading cause of cancer mortality worldwide. Current treatment for colorectal cancer only has limited success, thus more effective therapeutic approaches for these patients are urgently needed. Development of targeted drug delivery system is necessary to effectively deliver anticancer drugs to a tumor. The development of novel methods for early detection and effective treatments for cancer is contingent on the identification of unique biomarkers on the surface of cancer cells and isolation of tumor-specific ligands with high binding affinity to these biomarkers. Peptide phage display is a powerful method used to identify peptides capable of binding to a specific cell type by whole-cell panning, resulting in internalization of the peptide that can function as a drug delivery vehicle when conjugated to nanoparticle. This allows the use of the peptide to deliver toxic payloads intracellularly to achieve therapeutic effect. However, identification of the target protein of targeting peptide is problematic because the binding affinities of the peptides are low and difficult to maintain the native binding interaction between targeting peptide and isolated target protein from whole membrane extracts.

Therefore, a heretofore unaddressed need exists in the art to address the aforementioned deficiencies and inadequacies, especially in connection with cancer targeting peptides.

SUMMARY OF THE INVENTION

In one aspect, the invention relates to a conjugate comprising: (a) an isolated or a synthetic targeting peptide of less than 15 amino acid residues in length, comprising an amino acid sequence having at least 90% identity to a sequence selected from the group consisting of SEQ ID NOs: 1, 2 and 3; and (b) a component, to which the targeting peptide is conjugated, the component being selected from the group consisting of a drug delivery vehicle, an anti-cancer drug, a micelle, a nanoparticle, liposomes, a polymer, a lipid, an oligonucleotide, a peptide, a polypeptide, a protein, a cell, an imaging agent, and a labeling agent. The targeting peptide is active in binding to a human colorectal cancer cell, but does not bind to a normal cell.

The aforementioned targeting peptide may be of 10, 11, 12, 13, or 14 amino acid residues in length, or even less than 10 amino acid residues in length provided that the peptide's function in targeting cancer cells is maintained.

In one embodiment of the invention, the component is a drug delivery vehicle. The drug delivery vehicle may be selected from the group consisting of liposomes, polymeric micelles, lipoprotein-based drug carriers, nanoparticle drug carriers, dendrimers, stem cells, and polypeptides.

In another embodiment of the invention, the targeting peptide may be conjugated to: (a) one or more drugs selected from doxorubicin and vinorelbine; or (b) an oligonucleotide or (c) an imaging agent. The imaging agent may be, but not limited to, a radioactive molecule, a radiopharmaceutical, or an iron oxide particle.

In another embodiment of the invention, the conjugate may further comprises at least one anti-cancer drug encapsulated within the drug delivery vehicle. The at least one anti-cancer drug may be selected from the group consisting of doxorubicin, vinorelbine, and any combination thereof. In another embodiment of the invention, the drug delivery vehicle is a liposome. The liposome may be PEGylated.

The peptide may comprise an amino acid sequence having at least 95% identity to the sequence selected from the group consisting of SEQ ID NO: 1, 2 and 3.

In another embodiment of the invention, the sequence of the peptide is selected from the group consisting of SEQ ID NO: 1, 2, and 3.

In another embodiment of the invention, the component is a labeling agent conjugated to the C-terminus of the targeting peptide. In this embodiment of the invention, the conjugate may further comprises: (a) a cancer cell, bound to the targeting peptide, wherein the C-terminus of the targeting peptide is conjugated to the labeling agent; and (b) a cross-linker cross-linking the cancer cell to the targeting peptide.

In another embodiment of the invention, the component in the aforementioned conjugate is a protein named alpha-enolase.

Further in another aspect, the invention relates to a composition comprising: (a) a therapeutically effective amount of the conjugate as aforementioned; and (b) a pharmaceutically acceptable excipient, carrier or vehicle.

Alternatively, the invention relates to a composition comprising: (a) a therapeutically effective amount of the conjugate as aforementioned, wherein the anti-cancer drug is doxorubicin; (b) a therapeutically effective amount of the conjugate as aforementioned, wherein the anti-cancer drug is vinorelbine; and (c) a pharmaceutically acceptable excipient, carrier or vehicle.

In another aspect, the invention relates to a method of treating cancer, comprising: administering to a subject having the cancer the composition as aforementioned.

In another embodiment of the invention, the cancer comprises alpha-enolase on the cell surface thereof. The cancer may be selected from the group consisting of colon cancer, breast cancer, gliomas, lung cancer, leukemia, hepatocellular carcinoma, esophageal cancer, head and neck cancer, pancreatic cancer, prostate cancer, testicular cancer, and ovarian cancer.

Further in another aspect, the invention relates to a method of treating a cancer cell, comprising: causing the cancer cell, either in vivo or in vitro, to be exposed to an effective amount of the conjugate as aforementioned. The cancer cell may be present in a subject, or present in a tissue specimen obtained from a subject. The cancer cell may over-expresses alpha-enolase.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 8 is a Table showing alignment of phage-displayed peptide sequences selected by HCT116. The SEQ ID NOs. assigned to the sequences from top to bottom are 3, 4, 5, 6, 7, 8, 9, 10, 11, 2, 1, 12, 13, 14, 15, 16, 17, 18, 19, 20, 21, respectively.

DETAILED DESCRIPTION OF THE INVENTION

Figure 1:
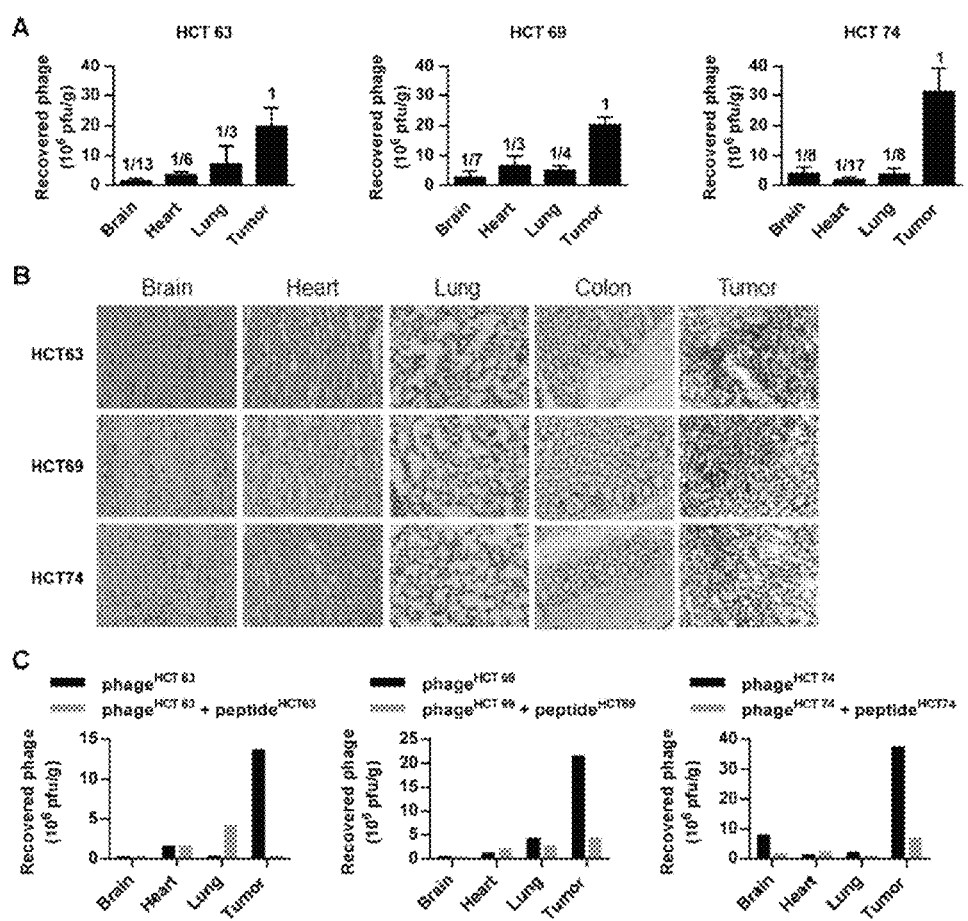
FIG. 1 shows verification of tumor-homing ability of selected phage clone in vivo. (A) NOD/SCID mice bearing HCT-116 xenografts were injected i.v. with selected phage clones. After 8 minutes, the free phages were washed out by PBS perfusion, and xenograft and organs were removed for determination of phage titer. (B) immunohistochemical detection of phage localization. Phage clones HCT-63, HCT-69 and HCT-74 showed strong accumulated in the tumor, but they were not detected in normal organs such as the brain, heart, lung and colon. (C) Targeting activity of phage clones to tumor tissues were competitively inhibited by their corresponding peptide.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a". "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein. "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "drug delivery vehicles" refers to a vehicle that is capable of delivering medication to a patient in a manner that increases the concentration of the medication in some parts of the body relative to others. Drug delivery vehicles includes, but not limited to, polymeric micelles, liposomes, lipoprotein-based drug carriers, nano-particle drug carriers, dendrimers, cells, polypeptides, etc. An ideal drug delivery vehicle must be non-toxic, biocompatible, non-immunogenic, biodegradable, and must avoid recognition by the host's defense mechanisms. The term "treating" or "treatment" refers to administration of an effective amount of the compound to a subject in need thereof, who has cancer, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The "Guidance for industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by calculations from the following formula:

$$HED = \text{animal dose in mg/kg} \times (\text{animal weight in kg/human weight in kg})^{0.33}.$$

Current treatment for colorectal cancer only has limited success due to the lack of pharmacoselectivity of the drugs to the diseased site. Thus, targeted drug delivery system is necessary to effectively deliver the anticancer drugs to the tumor. We have successfully identified specific peptides binding to the human colorectal carcinoma (hCRC) cells through in vitro biopanning using phage-displayed peptide library. Three high affinity phage clones to colorectal carcinoma were identified, and their binding activities were confirmed by cellular ELISA and flow cytometry. The hCRC-targeted phages recognized five colorectal carcinoma cell line and colorectal carcinoma surgical specimens from patients. The tumor homing ability of hCRC-targeted phages was confirmed by xenograft model in vivo. To investigate whether hCRC-targeted peptides could be used to enhance the therapeutic efficacy of anti-cancer drugs, we synthesized the peptide-mediated liposome encapsulated doxorubicin (pHCT74-LD) or vinorelbine (pHCT74-sLV). Notably, hCRC-targeted peptides conjugated liposomal drugs markedly inhibited hCRC tumor growth in mouse xenograft models. Combination treatment of pHCT74-LD and pHCT74-sLV was able to completely eradicate tumors in three-sixth of the total number of tumor-bearing mice without any signs of recurrence. Biodistribution studies in tumor-bearing mice indicated that chemotherapeutic drugs were localized in tumor tissue following administration of hCRC targeting peptides conjugated liposomal doxorubicin. Our findings indicate that hCRC-targeted peptides have great potential to be developed into targeted drug delivery systems and imaging for cancer including, but not limited to, colorectal carcinoma.

The invention relates to the discovery of targeting peptide and target protein on colorectal cancer cells by using biotinylated peptide to directly bind to intact cells, while using affinity trapping method and LC/MALDI-MS/MS to identify the unknown target protein on the plasma membrane of the cells. We disclose how phage libraries can be directly selected on tumor cell lines to generate peptides, which were able to bind to cell-surface receptors and were rapidly internalized upon binding. We also demonstrated the use of phage-displayed peptide in identifying the tumor antigen by affinity trapping method and LC/MALDI-MS/MS. Evaluation of tumor and organ distribution profiles of the peptide-targeted and non-targeted liposomes and the antitumor activity of the peptide-targeted liposomal drugs on mice bearing xenografts of human colorectal carcinoma were performed. The combination of targeted nanomedicine showed enhanced antitumor effect and markedly extended survival of mice with orthotopic human colon cancer, suggesting great potential to be developed into targeted drug delivery systems for cancer therapy. Phage clones and displayed peptide sequences are listed in FIG. 8. The SEQ ID NOs. are as follows:

| HCT-74: | SSMDIVLRAPLM; | (SEQ ID NO: 3) |
| HCT-01: | AAPELVAPSIWL; | (SEQ ID NO: 4) |
| HCT-40: | SLSLVAPVLSLL; | (SEQ ID NO: 5) |
| HCT-70: | TMGFTAPRFPHY; | (SEQ ID NO: 6) |
| HCT-50: | SPGLSLVSHMQT; | (SEQ ID NO: 7) |
| HCT-41: | LTRPNGIPHLSL; | (SEQ ID NO: 8) |
| HCT-21: | TSYSINLLSTPM; | (SEQ ID NO: 9) |
| HCT-10: | SPTGLFMTLSSR; | (SEQ ID NO: 10) |
| HCT-04: | HHRTLSPSVSIL; | (SEQ ID NO: 11) |
| HCT-69: | TSVSIVSTVLTP; | (SEQ ID NO: 2) |
| HCT-63: | RLNLDIIAVTSV; | (SEQ ID NO: 1) |
| HCT-08: | LATPFTATSATG; | (SEQ ID NO: 12) |
| HCT-71: | VTSSLPRMFHTL; | (SEQ ID NO: 13) |
| HCT-12: | GFLPLPRGEIFS; | (SEQ ID NO: 14) |
| HCT-92: | TPSLPPTMFRLT; | (SEQ ID NO: 15) |
| HCT-59: | GHLIPLRQPSHQ; | (SEQ ID NO: 16) |
| HCT-47: | SPNFSWLPLGTT; | (SEQ ID NO: 17) |
| HCT-33: | KVDAGLGSIFLL; | (SEQ ID NO: 18) |
| HCT-34: | WGITVETAYGTA; | (SEQ ID NO: 19) |
| HCT-35: | SELHVRLSHINA; | (SEQ ID NO: 20) |
| HCT-45: | SSGGVRWSAHWS. | (SEQ ID NO: 21) |

Illustrations of Industrial Applications

The targeting peptide (e.g., pHCT74 peptide) may be linked to an anti-cancer drug via a chemical linker just like ADC (antibody drug conjugate). Potential applications of the targeting peptides include, but not limited to, the following:

Peptide conjugates of oligonucleotides. Synthesis and applications of peptide oligonucleotide are already known in art (Venkatesan et al. "Peptide Conjugates of Oligonucleotides: Synthesis and Applications" Chem. Rev. 2006, 106, 3712-3761).

Peptide conjugated micelle (Layek et al. "Cell Penetrating Peptide Conjugated Polymeric Micelles as a High Performance Versatile Nonviral Gene Carrier" Biomacromolecules 2013, 14, 4071-4081).

Peptide-drug conjugates: peptide-drug-conjugates (Arap et al. "Cancer treatment by targeted drug delivery to tumor vasculature in a mouse model" Science 1998, 279(5349):377-80; Forner et al. "Peptide-drug conjugates: types, utility & Manufacturing" Specialty Chemicals Magazine May 2012, p 46-47; Firer et al. "Targeted drug delivery for cancer therapy: the other side of antibodies" Journal of Hematology & Oncology 2012, 5:70; Majumdar et al. "Peptide-Mediated Targeted Drug Delivery" Medicinal Research Reviews 32, No. 3, 637-658, 2012; Zhang et al. "Cellular Uptake and Cytotoxicity of Drug-Peptide Conjugates Regulated by Conjugation Site" Bioconjugate Chemistry 2013, 24, 604-613; Lelle et a. "Novel cleavable cell-penetrating peptide-drug conjugates: synthesis and characterization" J. of Peptide science 2014; 20: 323-333).

Peptide-Polymer Conjugates: Annu Rev Phys Chem. 2013; 64:631-57; Cancer vaccines: (Arens et al. "Prospects of combinatorial synthetic peptide vaccine-based immunotherapy against cancer" Seminars in Immunology 25 (2013) 182-190).

Peptide conjugated to magnetic nanoparticle: (Xie et al. "Surface-engineered magnetic nanoparticle platforms for cancer imaging and therapy" Accounts of Chemical Research 44(10) 883-892, 2011).

Peptide-dendrimer conjugates: (Liu et al. "Novel peptide-dendrimer conjugates as drug carriers for targeting non-small cell lung cancer" International J. of Nanomedicine 2011:6 59-69).

Radiolabeled Peptides: (Fani et al. "Radiolabeled Peptides: Valuable Tools for the Detection and Treatment of Cancer" Theranostics 2012, 2(5): 481-501).

Peptide conjugates for cancer molecular imaging such as $Fe_3O_4$: Anticancer Agents Med Chem. 2012; 12(5):476-99.

Several functional groups on the doxorubicin have been used for conjugation to the peptides. The primary amine can be directly linked to a carboxylic acid group of the C-terminal or the Asp side chain on the peptide carrier. Drug-peptide conjugation via an amide bond is carried out by linking the carboxylic acid of the drug and primary amine of the spacer/peptide. For amide bond formation, the carboxylic acid on the spacer, peptide, or the drug can be activated with O-benzotriazole-N,N,N',N'-tetramethyl-uronium-hexafluorophosphate (HBTU) or a mixture of 1-ethyl-3-(3-dimethylaminopropyl) carbodiimide hydrochloride (EDC) and N-hydroxybenzotriazole (HOBT). The activated carboxylic acid is then reacted with an amine group of the counterpart (i.e., drug or peptide) in the presence of a strong base (i.e., diisopropylethylamine or triethylamine) in different solvents, including dimethylformamide or dimethylsulfoxide to give the desired conjugate. To provide a spacer between the doxorubicin and the peptide carrier, the amino group is reacted with succinic or glutaric anhydride to give a product with a free carboxylic acid group, which can be linked to a free amino group on the peptide. The primary alcohol at the C14 of doxorubicin has been linked to a carboxylic acid group on the carrier molecule via an ester bond. The C13 ketone group on doxorubicin is also reacted to hydrazine to form a hydrazone spacer that is linked to the peptide carrier.

The ester linkage is commonly used to conjugate drug to peptide because it can be hydrolyzed chemically or enzymatically (i.e., esterase) to release the drug. To conjugate doxorubicin to peptide, C14 of doxorubicin was modified with glutaric ester and the other carboxylic acid of the glutarate was linked to the side chain amino group of D-Lys on the peptide to give doxorubicin-peptide conjugate.

A hydrazone linkage can be utilized as an acid-labile bond for releasing the drug molecule from the conjugate upon a decrease in pH in tumor extracellular environments and in the lysosomes. Daunorubicin and doxorubicin with a ketone functional group at C-13 were derivatized with hydrazine maleimido spacers (i.e., m-maleimidobenzoic acid hydrazine or p-maleimidophenylacetic acid hydrazine) to give hydrazide intermediates. These maleimide intermediates were reacted with the thiol group of the Cys residue in the peptide to give the respective conjugates. The presence of an aromatic ring on the spacer provided the possibility to regulate the stability of the hydrazone bond.

Camptothecin and combretastatin were conjugated to peptides using a carbamate bond between the drug and the spacer. The spacer contained a methyl-aminoethyl moiety that was attached to the carbamate nitrogen as a "built-in-nucleophile assisted releasing" (BINAR) moiety, which acted as a nucleophile to release camptothecin. This secondary amine of the BINAR moiety attacked the carbonyl carbon of the carbamate group to form a five-membered ring urea on the spacer: this was followed by the release of the drug into the medium.

The peptides were conjugated to doxorubicin with 1-ethyl-3-(3-dimethyl-aminoproproyl) carbodiimide hydrochloride (EDC) and N-hydroxysuccinimide (NHS). The conjugates were freed of reactants by gel filtration on a Sephadex G25. The carbodiimide conjugation method precluded a determination of the stoichiometry of the conjugates by mass spectrometry (Science 1998, 279(5349):377-80).

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Cell Lines

HCT116, HT29, LS174T, SW620, COLO 205, A498, HTB-10, B16F10, SKOV3, PC3, U2OS, 1112SK, H184, SAS, H460, MIA PaCa2, SK-HEP-1, and Mahlavu cells were purchased from American Type Culture Collection (ATCC) and were authenticated by ATCC based on DNA profile, cytogenetic analysis and isoenzymology. These cells were cultured in accordance to ATCC's protocols and were passaged for fewer than 6 months after resuscitation.

Phage Display Biopanning Procedures

Phage-displayed random peptide library (New England Biolabs, MA USA) based on a combinatorial library of random peptide 12-mers fused to a pIII coat protein of M13 phage was used in our experiments. HCT116 cells were grown to 70-80% confluence. The growth medium was removed and washed two times with serum free DMEM. It was then blocked with blocking buffer (serum free DMEM containing 1% BSA) at 4° C. for 30 min. The $2\times10^{11}$ pfu of phage-displayed peptide library was added to HCT116 cells. The cells with reaction mixture were incubated on shaker at 4° C. for 1 hr. After incubation, the cells were washed 4 times with PBS to remove unbound phages. The phages that bound to cells were recovered with lysis buffer (50 mM Tris-HCl, pH 7.4, 150 mM NaCl, 1% Nonidet P-40). The recovered phages were amplified and titrated with *Escherichia coli* ER2738 culture (New England BioLabs, MA, USA). Amplified phages were subjected to next round of biopanning using HCT116 cells. The 5th round phage eluates were titrated on LB/IPTG/X-Gal plates for phage clone identification.

Identification of Phage Clones by ELISA

The selected phages were further identified by ELISA screening. $1\times10^4$ cells were seeded into each well of 96-well ELISA plates (Falcon, Calif., USA) overnight and were fixed with 2% paraformaldehyde or methanol/acetone (1:1) for 10 min at RT. The plates were washed twice with PBS and were blocked with 1% BSA in PBS (w/v) for 30 min at RT. Then individual phage clones were added and incubated for 1 hr at RT. Following washing three times with PBS, the plates were incubated with horseradish peroxidase (HRP)-conjugated mouse anti-M13 phage antibody (GE Healthcare) at 1:2000 dilution for 1 hr at RT. The plates were washed three times with PBS again, and were subsequently incubated with the peroxidase substrate o-phenylenediamine dihydrochloride (OPD; Sigma) plus $H_2O_2$. The reaction was terminated by 3 N HCl, and the absorbance was measured using microplate reader (Model 680, BioRad) at 490 nm.

Flow Cytometry Analysis

Cells were grown to 70-80% confluence and were harvested with 10 mM EDTA in PBS. Peripheral blood mononuclear cells were prepared by using Ficoll-Paque Plus density gradient separation. After washing and suspending the cells with FACS buffer (PBS containing 1% fetal bovine serum), the cells were incubated for 1 hr at 4° C. with $5\times10^9$, $1\times10^9$ cfu individual phage clones or control phage, respectively. After washing twice with FACS buffer, cells were incubated with mouse anti-M13 monoclonal antibody (GE Healthcare) at 1:2000 dilution for 1 hr followed by 30 min with phycoerythrin (PE)-conjugated goat anti-mouse secondary antibody (Jackson ImmunoResearch) at 1:250 dilution at 4° C. The emission fluorescence signals were measured using FACSCantoII (Becton Dickinson) and were analyzed by FlowJo software.

Identification of Phage DNA Sequences

The selected phage clones were amplified and precipitated by 1/6 volume of polyethylene glycol (PEG)-NaCl [20% (wt/vol) PEG 8000 and 2.5M NaCl]. The phage pellet was resuspended in 100 μl of iodide buffer (10 mM Tris-HCl pH 8.0, 1 mM EDTA, 4 M NaI) and was incubated with 250 μl of 100% ethanol at room temperature for 10 min. Phage DNA was isolated after centrifugation, washed with 70% ethanol, air dried, and resuspended with 50 μl double distilled water. The DNA sequences of purified phages were determined by di-deoxynucleotide chain termination method using an automated DNA sequencer (ABI PRISM 377, Perkin-Elmer, CA, USA). The sequencing was performed with the -96 gIII sequencing primer 5'-CCCTCATAGTTAGCGTAACG-3' (SEQ ID NO: 23) corresponding to the phage minor coat protein pIII gene sequence.

Animal Model for In Vivo Targeting and Competition Assay

Non-obese diabetic-severe combined immunodeficiency (NOD/SCID) mice were injected subcutaneously (s.c.) into the dorsolateral flank with $5\times10^6$ HCT116 cells. When the xenograft tumor size reached 300±50 mm³, the mice were injected intravascularly (i.v.) with $2\times10^{11}$ pfu of the targeting phage or control phage M13KO7. Seven min after injection, the mice were sacrificed and perfused through the heart with 50 mL of PBS to wash unbound phages. After perfusion, xenograft tumor and mouse organs were taken out, washed three times with cold PBS, and cut into pans, with some of them homogenized. The phages bound to each tissue sample were recovered by log-phase *Escherichia coli* ER2738 culture and were titered on LB/IPTG/X-Gal agar plates. In peptide competitive inhibition experiments, $2\times10^9$ pfu of phage was co-injected with 100 μg of corresponding peptide or an unrelated control peptide.

Immunohistochemical Localization of Phages in Xenograft Tumor Mass

The tissue samples from in vivo phage homing experiment were embedded in frozen blocks. To evaluate the phage distribution in each tissue by immunohistochemistry, the frozen specimens were cut to 8-μm-thick sections and were collected on coated slides. The slides were washed with cold PBS to remove OCT and were fixed with 4% paraformaldehyde for 10 min at RT. To block endogenous peroxidase activity, the slides were soaked with 3% hydrogen peroxide in methanol for 30 min at RT. The nonspecific antibody binding sites were blocked by immersing the section with 1% BSA in PBS for 30 min at RT. The tissue sections were incubated with mouse anti-M13 monoclonal antibody at 1:250 dilution for 1 hr, followed by adding Super Enhancer reagent (Super SENSITIVE™ Polymer HRP Detection System/DAB, BioGenex) for 20 min and Poly-HRP reagent (BioGenex) for 30 min. After washing, the sections were developed with DAB (3,3'-diaminobenzidine) Chromogen (BioGenex) supplemented with Stable DAB buffer. The reaction was stopped by adding PBS. For nuclei staining, the slides were immersed in hematoxylin for 5 min, and were then mounted with mounting solution to terminate the reaction. The images of sections were taken and analyzed using automated acquisition system (TissueGnostics).

Tumor Binding Analysis of Phage Clones by Immunohistochemistry

Human colorectal carcinoma surgical specimens were obtained from the archives of Department of Pathology, National Taiwan University Hospital. The OCT-embedded frozen tissue blocks were cut into 8-μm-thick tissue sections, collected on coated slides, and fixed with 2% paraformaldehyde for 10 min at RT. 3% hydrogen peroxide in methanol was added to the slides for 30 min, followed by blocking with 1% BSA in PBS for 30 min. The samples were incubated with mouse anti-M13 monoclonal antibody at 1:200 dilution for 1 hr, followed by adding Super Enhancer reagent (SUPER SENSITIVE™ Polymer HRP Detection System/DAB, BioGenex) for 20 min and Poly-HRP reagent (BioGenex) for 30 min. After washing, the sections were developed with DAB (3,3'-diaminobenzidine) Chromogen (BioGenex) supplemented with Stable DAB buffer, and the reaction was stopped by adding PBS. For nuclei staining, the slides were immersed in hematoxylin for 5 min. and were subsequently mounted with mounting solution to terminate the reaction. The images of sections were taken and analyzed using automated acquisition system (TissueGnostics).

Peptide Synthesis and Labeling

The peptides were synthesized on a CEM Liberty automated microwave peptide synthesizer (Matthews, N.C., USA) using standard Fmoc-based solid phase chemistry, HOBt/HBTU activation, and Wang resin (0.55 meq/g substitution). Biotinylated versions of the peptides included an additional N-terminal or C-terminal biotin and a Gly-Gly-Gly spacer. The peptides were N-terminally biotinylated with biotin p-nitrophenylester (biotin-ONp). Biotin NOVATAG™ resin was used for the synthesis of C-terminus biotinylation peptides. The deprotection reaction was carried out by adding 7 ml of 20% piperidine in DMF in two stages with an initial deprotection of 30 sec at 45° C., followed by 3 min at 75° C. Coupling reactions were achieved with 5 equivalents of Fmoc-AA-OH with 1:1:1 AA/DIC/Oxyma for 5 min at 75° C. After completion of the synthesis, the peptide was cleaved from the resin with TFA/TIS/water (95:2.5:2.5) for 2.5 hrs at room temperature, and then was precipitated and washed by addition of cold diethyl ether.

Synthesis of Peptide-PEG-DSPE Conjugates

N-hydroxysuccinimido-carboxyl-polyethyleneglycol (MW, 3400-derived distearoylphosphatidyl ethanolamine (NHS-PEG-DSPE; 8.5 mg) dissolved in 0.25 ml of dichloromethane was added to 0.25 ml of DMSO containing 3.1 mg of peptide. It was then mixed with 0.011 ml of triethylamine to catalyze the reaction. The stoichiometric molar ratio of peptide and NHS-PEG-DSPE was 1.1:1. The reaction was carried out for 72 hours at room temperature. The peptide-PEG-DSPE conjugates were purified by dialysis with a 2 kDa cut-off membrane (Spectrum), and were then dried through lyophilization.

Cell Viability Assay

Cells were seeded in 96-well plates 1,000 per well and incubated with drug in culture medium at varying concentrations at 37° C. for 72 hrs. The cell viability was detected by MTT assay according to manufacturer's instruction. Each assay was repeated four times. The data were presented as the percent of viable cells compared with that of untreated control cells.

Preparation of Peptide-Liposomal Drugs

A lipid film hydration method was used to prepare PEGylated liposomes composed of distearoylphosphatidylcholine, cholesterol, and mPEG$_{2000}$-DSPE, which were then used to encapsulate doxorubicin (3:2:0.3 molar ratio) or vinorelbine (3:2:0.15 molar ratio). The lipid film were hydrated at 60° C. in 250 mM ammonium sulfate or 300 mM ammonium salts of 5-sulfosalicylic acid solution, and were extruded through polycarbonate membrane filters of 0.1 μm pore size using high-pressure extrusion equipment (Lipex Biomembranes, Vancouver, British Columbia) at 55° C. Doxorubicin and vinorelbine were encapsulated by a remote loading method at a concentration of 1 mg of doxorubicin and 3.5 mg of vinorelbine per 10 μmol of phospholipid. The final concentration of liposome was estimated by phosphate assay. The peptide-PEG-DSPE was subsequently incorporated into pre-formed liposomes by co-incubation at 60° C., the transition temperature of the lipid bilayer, for 0.5 hour with gentle shaking Sepharose 4B (GE Healthcare) gel filtration chromatography was used to remove released free drug, unconjugated peptides, and unincorporated conjugates. Doxorubicin concentrations in the fractions of eluent were determined by measuring fluorescence at $\lambda Ex/Em=485/590$ nm using a spectrofluorometer (Spectra Max M5, Molecular Devices). Vinorelbine concentrations were determined using the HPLC method.

Identification of the pHCT74 Peptide Binding Protein

HCT116 cells were grown to 70-80% confluence and were harvested with 10 mM EDTA in PBS. The biotinylated pHCT74 peptide was added to the cells and incubated for 1 hour at 4° C. After incubation, cells were washed with ice-cold PBS, and the DTSSP solution was added to a final concentration of 2 mM. The reaction mixture was incubated on ice for 2 hours. The reaction was stopped by the addition of 20 mM Tris-HCl. The plasma membrane lysates were prepared using the MEM-PER® Eukaryotic Membrane Protein Extraction Reagent Kit, (Thermo Fisher Scientific, Rockford, Ill., USA) according to the manufacturer's instructions. DYNABEADS® MYONE® Streptavidin C1 (Invitrogen, CA, USA) was added to the above protein lysates and mixed thoroughly. Immuno-magnetic separation was used to pull down the peptide-protein complexes. Finally, the purified proteins were separated by SDS-PAGE and silver-stained with a SILVERQUEST™ Silver Staining Kit (Invitrogen, CA, USA). The protein band was digested with trypsin, and the peptide fragments were identified by LC/MS/MS. Proteins were identified by searching Swiss Protein Database using the Mascot (Matrix Science, London, UK) and TurboSequest search engines (Thermo Fisher Scientific, Rockford, Ill., USA).

In Vivo Tumor Targeted Therapeutic Studies

Cancer cells ($5\times10^6$) were injected subcutaneously into dorsal-lateral flank of the female NOD.CB17-Prkdc$^{scid}$/J mice (4-6 weeks old). The mice bearing xenografts were then randomly assigned into several groups for different treatments. Drug was administered twice a week through tail vein injection for four consecutive weeks. Body weights and the tumor sizes were measured by electronic scale and calipers. The tumor volumes were calculated using the equation:

length×(width)²×0.52. At the end of the experiment, tumor mass of each mouse and their visceral organs such as brain, lungs, heart, liver, and kidney were removed and embedded with OCT for further histopathological examination. Animal care was carried out in accordance with guide lines of Academia Sinica, Taiwan.

Orthotopic Implantation and Therapeutic Studies

The orthotopic implantation methodology has been described in detail in earlier reports (Tseng et al., 2007). The HCT116 cells were infected with Lenti-luc virus (lentivirus containing the luciferase genes). NSG mice (NOD.Cg-Prkdc$^{scid}$ Il2rg$^{tmIWjl}$/SzJ) were used for orthotopic implantation. The mice were anesthetized using i.p. injection of Avertin, 2,2,2-Tribromo-ethanol (SIGMA Chemical Co) at a dose of 250 mg/Kg. For orthotopic implantation procedures, a 1-cm laparotomy was performed, and both the caecum and ascending colon were exteriorized. Exponentially growing HCT116-Luc cells (luciferase-expressed HCT116 cells) were inoculated into the cecal wall. The bowel was then returned to the peritoneal cavity and the abdomen was closed with absorbable 5-0 vicryl suture and skin with 5-0 proline suture. Tumor development was monitored using bioluminescence imaging. For orthotopic therapeutic study, mice were then treated with different formulations of anti-cancer drugs. Tumor progression monitored by bioluminescence quantification. Mouse body weight and survival rate were measured. Animal care was carried out in accordance with the guidelines of Academia Sinica, Taiwan.

Statistical Analyses

We analyzed phage titer, tumor volume, body weight, and doxorubicin concentration data using two-sided unpaired Student's t-test. We considered a P value below 0.05 as significant for all analyses. Values are represented as mean±standard deviation (S.D.).

Results

Identification of Colorectal Carcinoma-Targeting Peptide Ligands by In Vitro Phage Display Screenings We performed in vitro panning starting from a phage-displayed 12-mer random peptide library using HCT116 cells as the target cells. After five rounds of affinity selection, the recovery rate of the fifth round had increased by 28.7-fold over that observed in the first round. Individual phage clones were randomly picked up from the fifth round of selection for further screening. We performed a first validation on 95 phage clones using ELISA assays with HCT116 cells. Fifty nine out of the ninety five selected phage clones showed weak or no binding. However, 36 phages displayed peptides were capable of high specific binding, compared to the control insertless phage (M13KO7 phage). Multiple sequence alignment software was used to compare peptide sequences obtained from candidate phages. The peptide motifs were identified in several groups of related sequences (FIG. 8, Table 1).

In order to rule out the possibility that the selected phages bind to secreted or intracellular protein of the target cells, the cell surface-binding activity was further verified by flow cytometry analysis. The results showed that seven of 36 phage clones reacted strongly with the surface receptors of HCT116 cells, whereas eight phage clones had moderate reactivity, with the rest exhibiting only weak reactivity. The phage clones with high surface-binding activity to HCT116 were selected for further in vive validation.

In Vivo Validation of Tumor-Homing Ability of Colorectal Carcinoma-Targeted Phage Clones To investigate the targeting ability of the selected phage clones in vivo, mice bearing HCT116 xenografts (300 mm³) were injected with 2×10¹¹ pfu of either the selected phages or control phage through the tail vein. Phages were circulated and then were perfused with PBS buffer to wash out non-specific binders in circulation. After perfusion, we recovered and determined the liters of phage in tumor masses and normal organs. The results showed that the three phage clones (HCT63, HCT69 and HCT74), but not the control phage, were significantly accumulated in the tumor mass, compared to that in the normal organs, such as brain, lungs and heart.

Furthermore, we verified the tissue distributions of the three selected phages with tumor homing experiments. The frozen tissue sections derived from the tumor and the normal organs were immunostained with anti-phage antibody. The results revealed that HCT63, HCT69 and HCT74 phages selectively localized in tumor tissues rather than in normal organ tissues, such as brain, heart, lungs and colon (FIGS. 1A and B). Not surprisingly, no immunoreactivity was detected in the case of control phage in the tumor and the normal organ tissues (FIG. 1B).

The tumor-homing ability of HCT63, HCT69 and HCT74 phages were further confirmed by peptide competitive inhibition experiment. Mice bearing HCT116 xenografts were co-injected with HCT63, HCT69 and HCT74 phages clones and the homologous cognate synthetic peptide; pHCT63, pHCT69 and pHCT74 peptides (SEQ ID NOs: 1-3, respectively), respectively. The results showed that the cognate peptides markedly inhibited the recovery of phage particles from tumor tissue (FIG. 1C).

Figure 2:
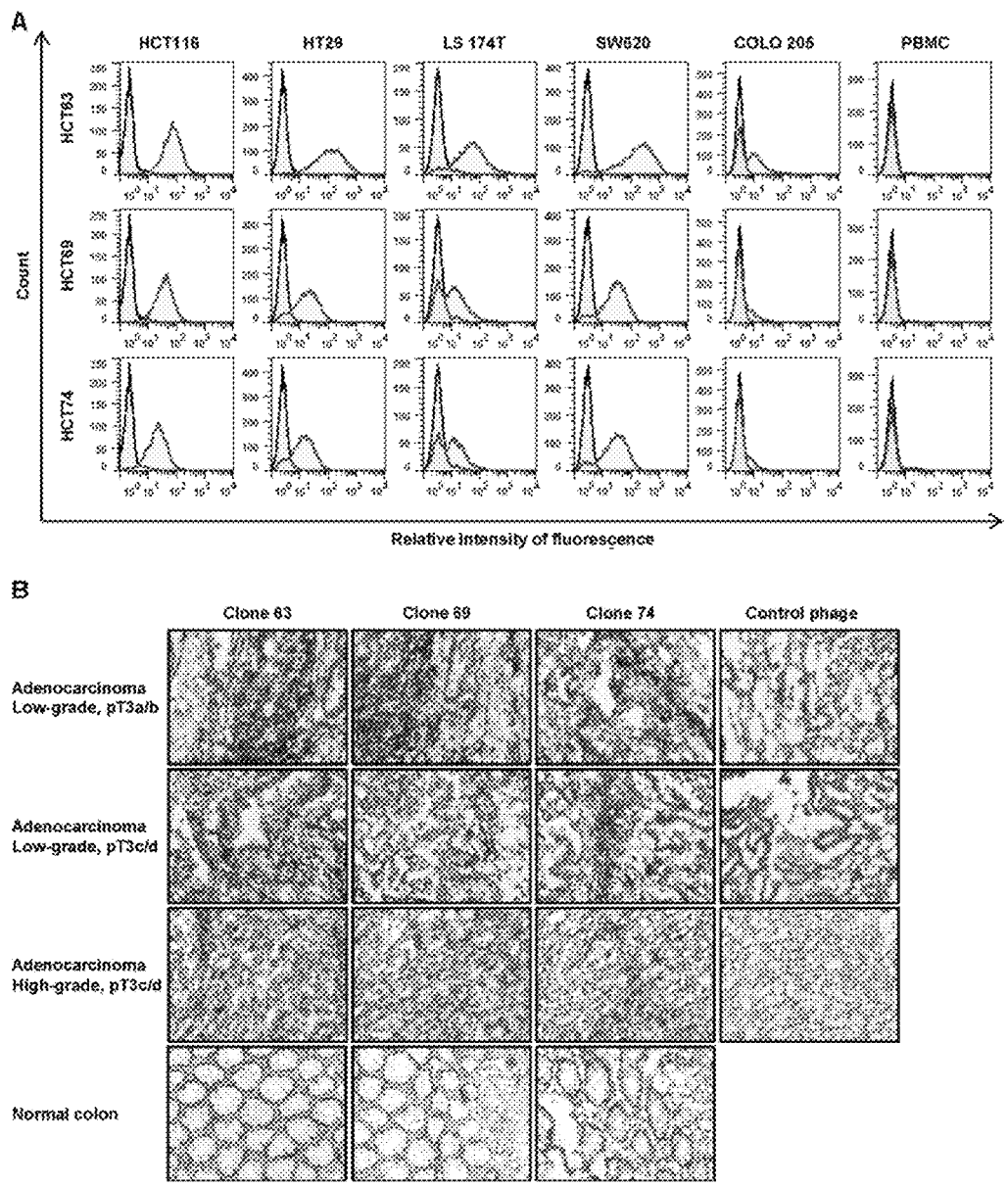
FIG. 2 shows binding activity of specific phage clone to various carcinoma cell lines and surgical specimens of hCRC biopsy. (A) Surface-binding activity of each clone to hCRC cells were determined by flow cytometry. Red: selected phage clone; black: control phage ($1 \times 10^{10}$ pfu/$2 \times 10^5$ cell). (B) Binding activity of specific phage clone to human colorectal carcinoma biopsy. Biopsy specimens from colorectal carcinoma patients incubated with phages were detected using anti-M13 phage antibody. The selected phages but control phages could detect surgical specimens of human colorectal carcinoma.

Validation of the Bindings of Selected Phage Clones to Various Human Cancer Cells To further investigate whether other human colorectal carcinoma (hCRC) cells can be recognized by each of the selected phage clones, five hCRC cell lines, including HCT116, HT29, LS174T, SW620 and COLO205, were incubated with selected phages, and their binding activities were analyzed by FACS. The results showed that the HCT63 phage reacted strongly with HCT116, HT29. LS174T, and SW620, but only moderately with COLO205 cells. HCT69 and HCT74 phages showed high binding affinity to HCT116, HT29, and SW620, moderate affinity to LS174T cells, and only weak affinity to COLO205 cell lines (FIG. 2A).

To confirm that the selected phage clones did not cross-react with normal cells, we examined the binding affinities between each selected phages and peripheral blood mononuclear cells (PBMC). The human PBMC were first isolated and incubated with each individual phage clone, and then were analyzed by FACS analysis. The results showed that all selected phages had no binding activity to PBMC (FIG. 2A). The HCT63, HCT69, and HCT74 phage clones were able to bind to hCRC cells but not to normal cells. These three phage clones were chosen for further study.

To evaluate the binding activities of the three selected phage clones to various human cancer cell lines, cellular ELISA was performed to detect sixteen types of human cancer cell lines, including A498, HTB-10, B16-F10, SKOV3, PC-3, U2OS, 1112SK, H184, SAS, H460, MIA Paca-2, HCT116, HUVAC, CL1-5, Mahlavu, and MDA-MB-231. The results showed that all three selected phages exhibited extensive binding activity to various cancer cell lines. HCT63 exhibited high binding specificity to all cancer cell lines, except HTB-10. HCT69 and HCT74 revealed highly specific binding to A498, B16-F10, SKOV3, PC-3, U2OS, 1112SK, H184, SAS, H460, MIA Paca-2, HCT116, HUVAC, Mahlavu, and MDA-MB-231, but only moderate binding to HTB-10 and CL1-5.

The binding specificity of the selected phages to hCRC cells was further tested using immunohistochemistry with surgical specimens from colorectal carcinoma patients. The results show that all three selected phages can recognize the tumor cells in the surgical specimens of colorectal carcinoma, but not their normal counterparts. The control phage reveals no immunoreactivity in the tumor tissues (FIG. 2B).

Production and Characterization of hCRC-Targeted Drug Delivery Nanocarriers

Figure 3:
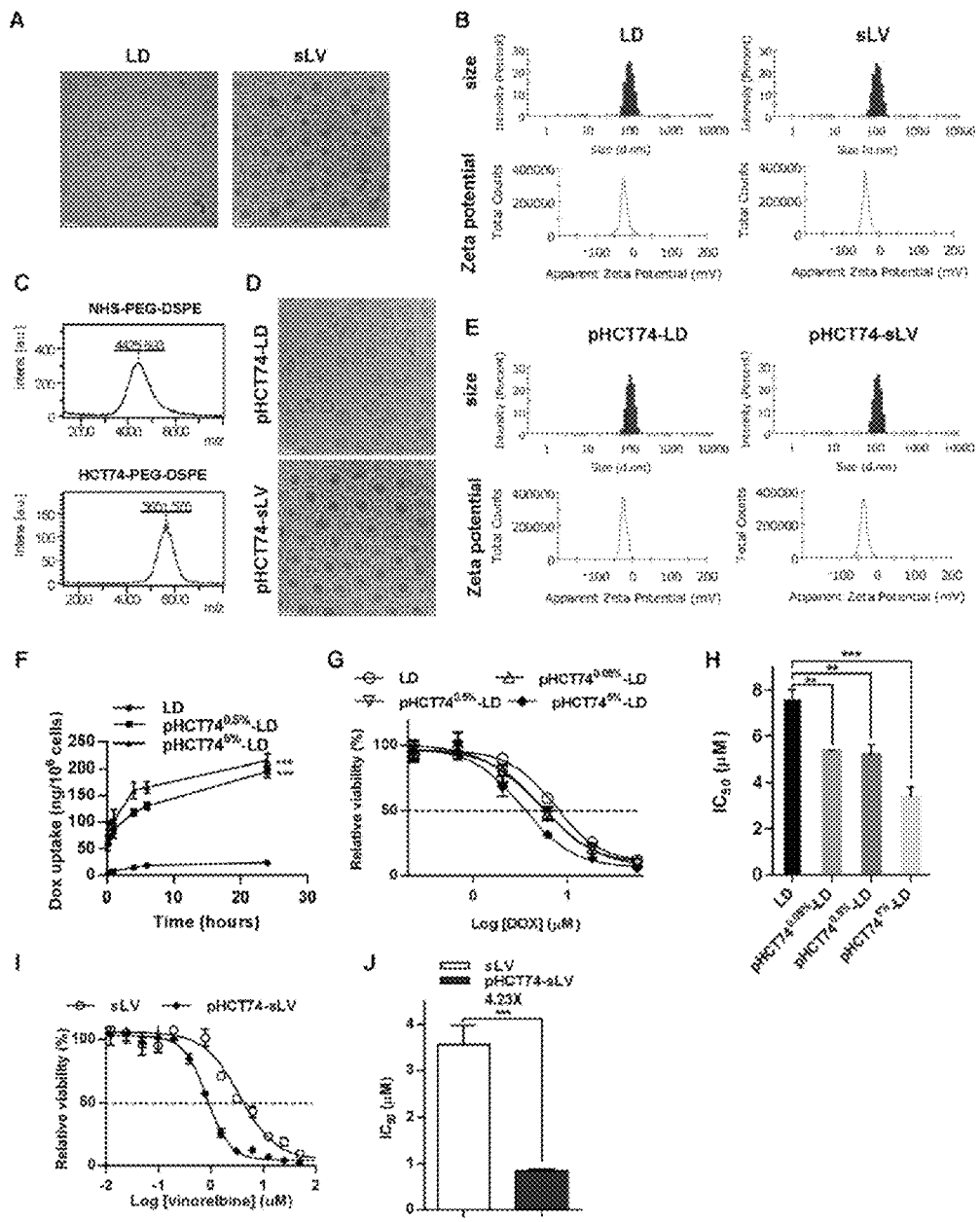
FIG. 3 shows targeted delivery of liposomal drug to hCRC cells. (A) Cryo-TEM micrographs of liposomal doxorubicin (LD) and stabilized liposomal vinorelbine (sLV). (B) Size distribution and zeta potential of LD and sLV. (C) MALDI-TOF mass spectrometric analysis of DSPE-PEG-NHS and DSPE-PEG-pHCT74 conjugate. (D) Cryo-TEM micrographs of pHCT74 peptide-conjugated LD and pHCT74 peptide-conjugated sLV (E) Size distribution and zeta potential of pHCT74-LD and pHCT74-sLV. (F) Doxorubicin uptake by HCT116 cells after incubation with different liposome formulations at 10 μg/ml. The doxorubicin quantified by fluorescence measurements of cell lysate samples. (G) In vitro cytotoxicity profiles of LD, or LD containing 0.05% to 5% (molar) pHCT74-peg-DSPE lipids using human HCT116 colorectal cancer cells. (H) The values of $IC_{50}$ were calculated using the GraphPad Prism software. (I) In vitro cytotoxicity profiles of vinorelbine, sLV, or pHCT74-sLV. (J) $IC_{50}$ values estimated for vinorelbine, sLV and pHCT74-sLV. Data shown are the means from 3 independent experiments. Bars, SD. (*, $0.05 \geq P > 0.01$; , $0.01 \geq P > 0.001$; and *, $P < 0.001$). The size scale bar represents 50 nm.

In order to find out effective chemotherapeutic agent to treat colorectal cancer, the cytotoxicity of several anticancer drugs were examined. Vinorelbine showed significantly better cytotoxicity profiles than other colon and rectal cancer drugs approved by the FDA. In this study, doxorubicin and vinorelbine were chosen to encapsulate by lipid-based nanoparticles. Liposomal doxorubicin is the first FDA-approved liposomal drug and most widely used member of the liposomal formulation of anticancer agents. Preparation of liposomal doxorubicin was achieved easily by following well-established protocol (FIGS. 3A and B). However, the same protocol could not be directly applied to develop liposomal vinorelbine due to its high membrane-permeability and different drug-retention properties. We successfully created a stable liposomal formulation of vinorelbine (sLV) with modified lipid composition and loaded vinorelbine with the ammonium 5-sulfosalicylate gradient method. Vinorelbine could be trapped and precipitated in the liposome (FIG. 3A). The mean particle size of liposome incorporated with different drugs as measured with the dynamic light scattering analyzer, was in the range of 9) to 110 nm (FIG. 3B). The zeta potential of liposome was in the range of −20 to −30 mV (FIG. 3B).

Because of specific binding affinity to hCRC cells and in vivo tumor-homing ability, peptide ligands displayed on the HCT63, HCT69, and HCT74 phages were chosen for subsequent studies. Their corresponding synthetic peptides were named pHCT63, pHCT69 and pHCT74, respectively. DSPE-$PEG_{3400}$-pHCT63 and DSPE-$PEG_{3400}$-pHCT74 were synthesized by coupling the peptide ligands to a commercially available NHS-activated pegylated lipid. The peptide-lipid conjugates were purified by lyophilization and dialysis, and were structurally confirmed by mass spectrometry. The major peaks of the pHCT63-$PEG_{3400}$-DSPE and pHCT74-$PEG_{3400}$-DSPE conjugates were centered at 5631.544 and 5651.576 mass-charge ratios, respectively, consistent with the calculated molecular weight of the peptide-lipid conjugates (FIG. 3C). The conjugates were then incorporated into a liposomal doxorubicin or liposomal vinorelbine via the post-insertion technique to perform hCRC-targeted liposomes. Morphology, size distribution and zeta potential of liposome were not significant changed after peptide post-insertion (FIGS. 3D and E), suggesting that the process did not alter the stability of this liposomal drugs.

In Vitro Targeting of Liposomal Drugs to hCRC Cells

To determine whether the synthetic pHCT63 and pHCT74 peptides have targeting activities, we examined the delivery efficiency of peptide bearing liposomes by measuring the amount of liposomal doxorubicin internalized into HCT116 cells. The doxorubicin-loaded liposomes post-inserted with various concentrations of peptide-$PEG_{3400}$-DSPE were incubated for various time periods. The kinetics of pHCT63$^{0.5\%}$-LD (with the ratio of peptide-$PEG_{3400}$-DSPE to phospholipid at 0.5% mole), pHCT63$^{5\%}$-LD, pHCT74$^{0.5\%}$-LD, pHCT74$^{5\%}$-LD, and non-targeted LD uptake by HCT116 cells were tested at 0.5th, 1th, 4th, 6th and 24th h time point (FIG. 3F). After incubating liposomes with cells and subsequently washing to remove any unbound nanoparticles, both the cells and the liposomes were lysed, and the amount of internalized doxorubicin was quantified by measuring total doxorubicin fluorescence.

The results showed that cells incubated for 24 hours with pHCT63$^{0.5\%}$-LD had a 2.1-fold increase in intracellular doxorubicin uptake compared with the non-targeted controls. As the ratio of pHCT63-$PEG_{3400}$-DSPE increased from 0.5% to 5%, the doxorubicin uptake increased from 2.1-fold to 5.2-fold, compared with LD under the same conditions. However, the pHCT74 targeting peptide markedly enhanced liposomal doxorubicin delivery to HCT116 cells. The uptake of pHCT74-LD increased more rapidly than pHCT63-LD during early incubation. The pHCT74$^{0.5\%}$-LD and pHCT74$^{5\%}$-LD demonstrated at most 11 to 16-fold more drug uptake than the non-targeted LD (FIG. 3F). This result indicates that low pHCT74 peptide density on the surface of liposome was sufficient for the improved delivery of the liposomes.

The pHCT74-LD significantly enhanced delivery of liposomes to hCRC cells in comparison with non-targeted control. Although pHCT63-LD also demonstrated the enhanced delivery to HCT116 cells, the improvement was moderate compared to pHCT74-LD. Significantly, the pHCT74 liposomes demonstrated higher delivery efficiency than pHCT63 liposomes. This result suggests that pHCT74 peptide is superior to pHCT63 peptide as targeting ligand for the delivery of liposomes to hCRC Cells.

It is reasonable to assume that increased cellular uptake would improve the cytotoxicity of liposomal doxorubicin. Thus, we sought to verify this hypothesis by comparing the cytotoxic effects of the various peptide bearing doxorubicin-loaded liposomes. As expected, pHCT63-LD and pHCT74-LD were more cytotoxic than the non-targeted liposomes, based on the results of drug accumulation (FIG. 3G). The $IC_{50}$ values determined for each liposome formulation are detailed in FIG. 3H. The $IC_{50}$ for pHCT63-LD and pHCT74-LD were approximately 2-fold lower than that for the non-targeted LD. More importantly, the $IC_{50}$ decreased with increasing peptide concentration. We also developed vinorelbine-loaded targeting liposomes. Expectedly, the pHCT74-sLV significantly enhanced drug cytotoxicity to HCT116 cells (FIG. 3I). The $IC_{50}$ for the pHCT74-sLV was 4.23-fold lower than that for the non-targeted sLV (FIG. 3J).

Pharmacokinetics and Biodistribution of hCRC-Targeted Liposomes

For pharmacokinetics analysis, pHCT74-LD and LD were administered to NOD.CB17-Prkdc$^{scid}$/J mice at matched 2 mg doxorubicin/kg through tail vein injection. Blood samples were withdrawn at selected time points, and the quantities of doxorubicin were analyzed. Fluorescent quantitative method for analysis was validated. The blood profiles, which declined progressively over time, were similar throughout the study for both pHCT74-LD and LD. The time course of pHCT74-LD and LD biodistributions to the tumor and various organs after the administration of the two liposomal drug formulations were examined. The maximum total doxorubicin concentration in tumor at 1.95±0.58 μg doxorubicin/g tumor occurred at 24 hours after pHCT74-LD administration and remained 1.60±0.99 μg/g at 72 hours. Maximum tumor accumulation of LD at 2 mg/kg (0.98±0.42 μg/g) occurred at 48 hours post-dose and gradually decreased with time to 0.73±0.18 μg/g at 72 hours post-injection. 1.95-fold higher tumor accumulation of pHCT74-LD compared to LD was observed at 24 hours. In contrast, distribution of pHCT74-LD in all non-malignant tissues was similar to that of LD at each time point. The tumor doxorubicin $AUC_{0-72}$ for pHCT74-LD was 106.69±36.13 μg h/g and the LD $AUC_{0-72}$ was 57.53±17.93 μg h/g, representing 1.85 times increase in doxorubicin $AUC_{0-72}$ for the treated mice.

To determine the amount of bioavailable drug in tumor cells, we performed whole body perfusion through the left ventricle of the heart with DPBS before biodistribution analysis. This operation can eliminate blood and liposomes remained in vessel and the interstitial space of tumors. After whole body perfusion, the tumor mass, brain, heart, lung, liver and kidneys were harvested and doxorubicin were quantified. We used intracellular accumulation of doxorubicin as an indicator of bioavailability of the liposomal drug. LD and pHCT74-LD were administered to tumor (HCT116)-bearing mice (NOD.CB17-Prkdcscid/J) at matched 1 mg doxorubicin/kg by i.v. injection. The doxorubicin levels were measured in the blood at different time points using fluorescent quantitative method. The blood profiles of both pHCT74-LD and LD were similar. Tumor uptake of pHCT74-LD at 1 mg/kg gradually increased before peaking at 0.76±0.14 µg/g at 24 hours post-dose and remained at 0.28±0.20 µg/g at 72 hours. Maximum tumor uptake of LD at 1 mg/kg (0.45±0.17 µg/g) occurred 24 hours post-dose and experienced almost no change over time at 0.18±0.06 µg/g at 72 hours post-injection. 1.69-fold higher uptake of pHCT74-LD compared to LD was observed at 24 hours. The tumor doxorubicin $AUC_{0-72}$ for pHCT74-LD was 35.17±6.50 µg h/g and the LD $AUC_{0-72}$ was 20.62±5.87 µg h/g, representing a 1.71 times increase in doxorubicin $AUC_{0-72}$ for the treated mice. The uptake of both drugs in most non-malignant tissues was low at the initial 1 hour post-injection. Liver and kidney uptake of both drugs gradually increased at 24 hours and then slowly declined thereafter.

Identification of the Target Protein of pHCT74 Peptide

Figure 4:
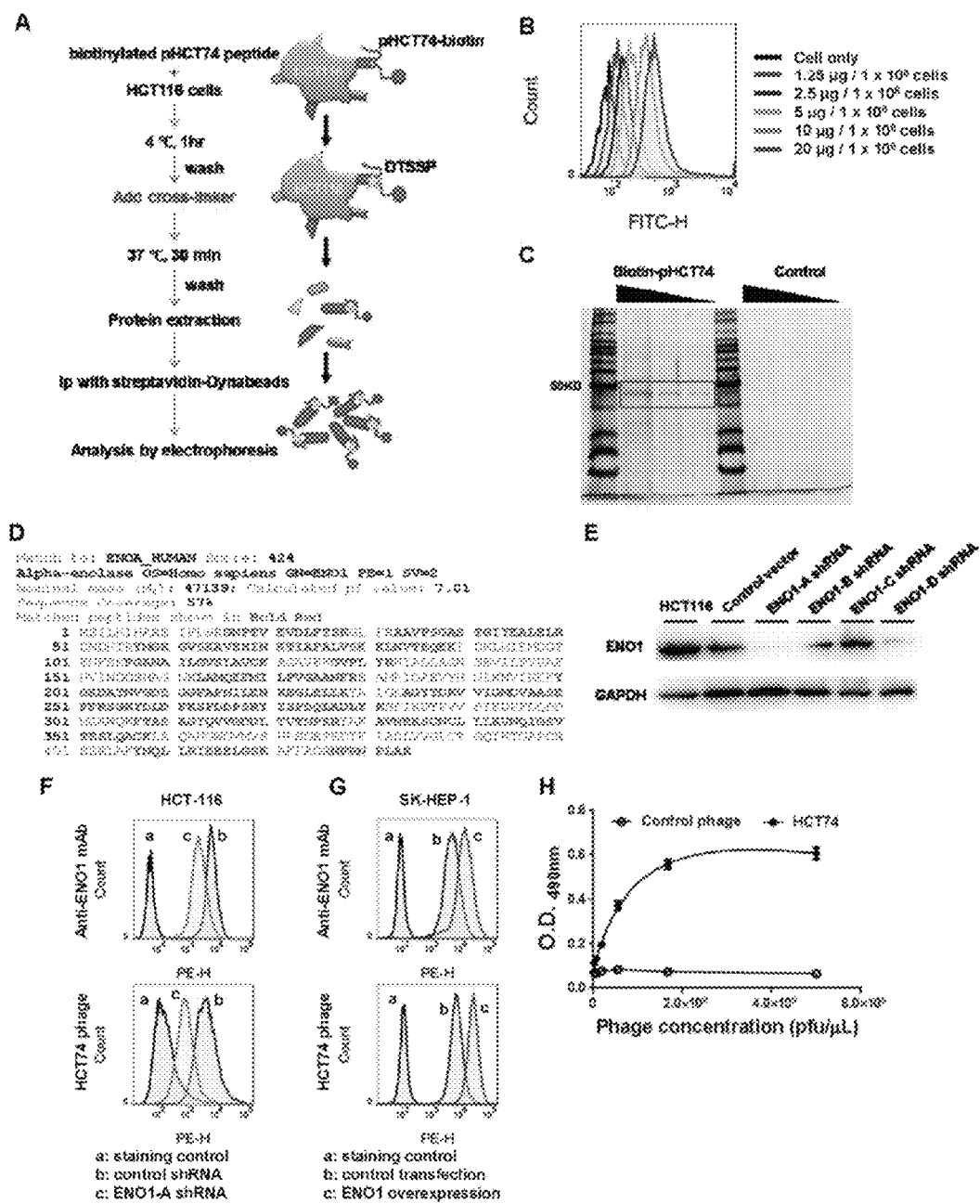
FIG. 4 shows identification of the target protein of pHCT74 peptide. (A) Schematic diagram of the experimental design. (B) The binding characteristics of biotinylated pHCT74 peptide to HCT116 cells were evaluated by flow cytometry. (C) Affinity cross-linking of biotinylated pHCT74 peptide to the surface proteins of HCT116 cells, cross-linked proteins were cleaved from streptavidin dynabeads using 2-mercaptoethanol. The bands were revealed by silver staining. (D) The peptide sequence (SEQ ID NO: 22) of target bands were deduced by tandem mass spectrometry. (E) Stable knockdown of ENO1 gene by introducing specific shRNA (ENO1-A, B, C and D shRNA) into HCT116 cells through infection with viral vectors. (F) The binding activity of HCT74 phage was reduced after α-enolase gene knockdown (G) The binding activity of HCT74 phage was enhanced when α-enolase was overexpressed. (H) Binding affinity of the HCT74 phage to recombinant α-enolase protein. The 96-well plate was pre-coated with 2 ug/mL α-enolase protein and incubated with increasing concentrations of HCT74 phage and then with HRP conjugated anti-M13 antibody. Data are presented as mean±standard deviation.

We propose the use of biotinylated pHCT74 peptide and a chemical cross-linker, DTSSP, to identify the unknown target protein on the plasma membrane of HCT116 cells. Schematic diagram of the experimental design was shown in FIG. 4A. A biotin molecule was conjugated to the C terminus of synthetic pHCT74 peptide. The binding characteristics of biotinylated pHCT74 peptide to HCT116 cells were evaluated by flow cytometry for analyzing the concentration dependency of the binding (FIG. 4B). This addition of a single biotin to the C terminus of the peptide did not affect its cell binding activity. The membrane proteins of HCT116 cells were bound with biotin-pHCT74 peptide, cross-linked by DTSSP; followed by SDS-PAGE separation and LC/MS/MS analysis. A sharp bands was detected by silver staining (FIG. 4C), and subsequently analyzed by LC/MS/MS after tryptic digestion. Twelve tryptic peptides were identified as alpha-enolase (ENO1) fragments by search algorithms based on MASCOT software. Coverage of the identified peptides was 57% of the alpha-enolase sequence and the probability score was 424 (FIG. 4D).

To further confirm alpha-enolase was the target proteins of the pHCT74 peptide, correlation between the binding activity of HCT74 phage and ENO1 expression was examined. We established stable cell lines expressing shRNAs targeting ENO1 gene (FIG. 4E) and tested the binding activity of HCT74 phage by flow cytometry. The binding activity of HCT74 phage was reduced after ENO1 gene knockdown (FIG. 4F). Instead, after transient overexpression of ENO1 gene, the binding activity of HCT74 phage was increased (FIG. 4G). In conclusion, the expression of ENO1 was consistent with the binding activity of HCT74 phage. In addition, HCT74 phage specific binding to the alpha enolase protein was also confirmed by direct ELISA assay (FIG. 4H).

Therapeutic Efficacy of Peptide-Targeted Liposomal Drugs in Human Colorectal Carcinoma Xenografts In vivo anti-tumor activities of peptide-targeted liposomal drugs were tested using HCT116 and SW620 colorectal cancer tumor-bearing mice. To evaluate the anti-tumor efficacy of systemically administered pHCT74-LD compared to LD, NOD.CB17-Prkdc$^{scid}$/J were inoculated s.c. with HCT116 and SW620 tumors. Mice bearing colorectal carcinoma xenografts (~100 mm$^3$) were assigned into four groups for different treatments: A, pHCT74-LD; B, FD; C, LD; and D, PBS. Treatments were administered through tail vein injection, 1 mg/kg every 3.5 days for eight doses with total cumulative dose of 8 mg/kg. On day 28 in the HCT116 xenograft model, compared to untreated controls, administration of pHCT74-LD significantly inhibited tumor growth by 80.1% (p<0.01), whereas the treatment with LD and FD inhibited tumor growth by 65.8% (p<0.01) and 44.6% (p>0.01), respectively (FIG. 5A). The tumor size of the LD group gradually increased to 1.72-fold that of the pHCT74-LD by day 28. By the end of the treatment, the final average tumor weight in mice treated with pHCT74-LD was 0.15 g. compared to 0.24 g in mice treated with LD and 1.1 g in mice injected with PBS buffer (FIGS. 5B and C). The inhibition of growth for pHCT74-LD was more significant than that for LD (p<0.01). A similar result was observed in treatments with SW620 xenograft. The tumor size for mice bearing SW620 xenografts treated with pHCT74-LD was significantly smaller than those treated with non-targeted LD (FIGS. 5D, E and F). The pHCT74-LD and LD groups did not have significant changes in body weight during treatment period.

The efficacy of vinorelbine-loaded pHCT74 targeted liposomes was also investigated on growth inhibition of HCT116 cells s.c. xenograft in NOD.CB17-Prkdc$^{scid}$/J mice. Treatments were administered through tail vein injection at 1.5 mg/kg every 3.5 days for eight doses, with total cumulative dose of 12 mg/kg. On day 28, compared to untreated controls, administration of pHCT74-sLV significantly inhibited tumor growth by 68% (p<0.01), whereas the treatment with sLV inhibited tumor growth by 34% (p<0.01) (FIG. 5G). The tumor size of the sLV group gradually increased to 2.1-fold that of the pHCT74-sLV by day 28. By the end of the treatment, the final average tumor weight in mice treated with pHCT74-LD was 0.21 g, compared to 0.45 g in mice treated with LD and 0.86 g in mice injected with PBS buffer (FIGS. 5H and I). The pHCT74-sLV inhibition of growth was more significant than sLV (p<0.01).

Effect of the Combination of Systemically Administered pHCT74-LD and pHCT74-sLV on HCT116 Xenograft Tumors in an In Vivo Mouse Model Next, we examined whether the pHCT74 peptide could improve the efficacy of combination therapy using doxorubicin and vinorelbine. We established HCT116 xenografts in 42 NOD.CB17-Prkdc$^{scid}$/J mice (6 mice per group). Once the tumor reached the size of 280 mm$^3$, we treated the mice every 3.5 days intravascularly (i.v.) with either vehicle (PBS), LD (1 mg/kg), sLV (1.5 mg/kg), both LD (1 mg/kg) and sLV (1.5 mg/kg), pHCT74-LD (1 mg/kg), pHCT74-sLV (1.5 mg/kg) or both pHCT74-LD (1 mg/kg) and pHCT74-sLV (1.5 mg/kg) for eight doses.

Both 1 mg/kg LD and 1.5 mg/kg sLV modestly inhibited tumor growth, but the combined treatment with LD and sLV resulted in a statistically significant suppression of tumor growth (FIG. 6A). On day 35, compared to untreated controls, administration of both LD (1 mg/kg) and sLV (1.5 mg/kg) inhibited tumor growth by 92.1%, whereas the treatment with LD and sLV inhibited tumor growth by 50.6% and 73.3%, respectively. Moreover, groups receiving pHCT74-targeted liposomal drugs had better tumor growth inhibition than all treatment groups with non-targeted liposomes. The administration of both pHCT74-LD (1 mg/kg) and pHCT74-sLV (1.5 mg/kg) significantly inhibited tumor growth by 97.4%, whereas the treatment with pHCT74-LD and pHCT74-sLV inhibited tumor growth by 67.5% and 83.1%, respectively. At the end of treatment, tumor tissues were dissected and weighed (FIGS. 6C and D). The final average tumor weight in mice treated with combination of pHCT74-LD and pHCT74-sLV was 0.038 g, compared to 2.46 g in mice injected with PBS buffer. The Combination therapy using pHCT74-LD and pHCT74-sLV markedly inhibited tumor growth by 98.4% compared to untreated controls. In addition, three-sixths tumor treated with combination of 1 mg/kg pHCT74-LD and 1.5 mg/kg pHCT74-sLV were eradicated (FIGS. 6E and 6D).

In many cancer cases in humans, the tumors are detected when they are large. Since combination treatment of pHCT74-LD and pHCT74-sLV is a candidate treatment strategy for hCRC, we examine the effects of this combination on the large tumor model. We treated mice bearing large HCT116 xenografts (650 mm$^3$) i.v. with either vehicle (PBS), LD (1 mg/kg), sLV (2 mg/kg), both LD (1 mg/kg) and sLV (2 mg/kg), pHCT74-LD (1 mg/kg), pHCT74-sLV (2 mg/kg) or both pHCT74-LD (1 mg/kg) and pHCT74-sLV (2 mg/kg) for eight doses. We subsequently analyzed tumor development by measuring the tumor volume (FIG. 6F). A similar result was observed in treatments with the large HCT116 xenograft model. Both 1 mg/kg LD and 2 mg/kg sLV modestly inhibited tumor growth, but combination treatment of LD and sLV resulted in a statistically significant suppression of tumor growth. Co-treatment of pHCT74-LD and pHCT74-sLV enhanced the inhibition of tumor growth as compared with liposomal drug alone. Furthermore, two-sixths tumor treated with combination of 1 mg/kg pHCT74-LD and 2 mg/kg pHCT74-sLV were completely eradicated in the large tumor animal model (FIG. 6F). The toxicity profiles of combination chemotherapy are comparable. During the experiments, no lethal toxicity or significant weight loss was observed among treated mice, suggesting that the treatments did not produce any apparent toxicity (FIGS. 6B and G). These results indicate that the therapeutic efficacy of combination of pHCT74-LD and pHCT74-sLV is significantly superior to that of other formulations in colorectal carcinoma xenograft models.

Therapeutic Potential of Combination Therapy in the Orthotopic Colorectal Carcinoma Model Models based on the injection of cancer cell lines subcutaneously may not accurately reproduce human colon cancer biology. To study the influence of colorectal microenvironment in response to therapy, we developed an orthotopic mouse model of colorectal cancer to recapitulate the tumor growth pattern seen in colon cancer patients. We investigated the anti-tumor potential of combination of pHCT74 targeted liposomal doxorubicin and liposomal vinorelbine in vivo via i.v. administration in an orthotopic model of human CRC using HCT116-Luc tumor stably expressing firefly luciferase. Orthotopic tumor growth was monitored non-invasively using bioluminescence imaging Prior to the first therapeutic injection (5 days after tumor cell implantation), growing orthotopic tumors were detected using bioluminescence imaging and found to be localized mainly in the colon and rectum (FIG. 7A).

Mice were treated with either vehicle alone (PBS), FD (1 mg/kg)+FV (2 mg/kg), LD (1 mg/kg)+sLV (2 mg/kg) or pHCT74-LD (1 mg/kg)+pHCT74-sLV (2 mg/kg) every other day for sixteen days. Bioluminescence was done twice per week to monitor tumor burden. Bioluminescence images revealed that there was significant inhibition of tumor growth in both LD (1 mg/kg)+sLV (2 mg/kg)-treated group and pHCT74-LD (1 mg/kg)+pHCT74-sLV (2 mg/kg)-treated group compared with the vehicle control group or FD (1 mg/kg)+FV (2 mg/kg) group (FIGS. 6A and B). Furthermore, the combination of pHCT74-LD and pHCT74-sLV therapy showed enhanced antitumor effect and extended survival of mice with orthotopic human colon cancer (FIGS. 7D and E). Kaplan-Meier survival curves of all groups are shown in FIG. 7D. At the end of the study, the median survival times for PBS, FD+FV, LD+sLV and pHCT74-LD+pHCT74-sLV treatment groups were 32, 37, 53.5 and 64.5 days, respectively (FIGS. 7D and E). A survival analysis by log-rank (Mantel-Cox) test revealed pHCT74-LD+pHCT74-sLV treatment significantly extended animal survival compared with PBS, FD+FV and LD+sLV (FIG. 7F).

In summary, we successfully identified specific peptides binding to the hCRC cells through in vitro biopanning using human colorectal carcinoma (hCRC) cell line. Three high affinity phage clones targeting colorectal carcinoma were identified, and their binding activities were confirmed by cellular ELISA and flow cytometry. The hCRC-targeted phages were proved to recognize five colorectal carcinoma cell lines and surgical specimens from colorectal carcinoma patient. The tumor homing ability of hCRC-targeted phages was confirmed by xenograft model in vivo. To investigate whether hCRC-targeted peptides could be used to enhance the therapeutic efficacy of anti-cancer drugs, we synthesized the peptide-mediated liposomes encapsulated doxorubicin and vinorelbine. Biodistribution studies carried out in tumor-bearing mice showed that following administration, hCRC targeting peptides conjugated to liposomal doxorubicin localize to tumor tissues. The hCRC-targeting peptide-conjugated liposomal drugs markedly inhibited hCRC tumor growth in mouse xenograft models, consistent with the biodistribution studies. We examined the therapeutic efficacy of the combination of doxorubicin and vinorelbine on HCT116 cells. Targeting liposomes mediated by pHCT74 peptides markedly increased therapeutic efficacy by enhancing drug delivery to the tumor site while reducing the relative availability of the toxic drug to normal cells.

The modification of liposome with pHCT74 peptide has identical plasma pharmacokinetics to the non-targeting liposome, suggesting that targeting liposome formulation is as stable as non-targeting liposome in blood. In addition, the pHCT74-mediated targeting liposomes enhanced drug accumulation in tumor tissues without affecting the drug delivery to noncancerous host tissues or enhancing host toxicity (FIGS. 6B, 6G and 7C).

Over the past decade, targeted drug delivery systems have been developed and studied extensively in preclinical in vitro and in vivo models, but only a few promising results have progressed to be used effectively in the clinical environment. In recent years, the clinical success of antibody-drug conjugates (ADCs) offers a promising strategy for developing highly effective anti-cancer drugs. ADCs consist of potent cytotoxic drugs linked to antibodies via chemical linkers. One of the major challenges facing most ADCs is their relatively low capacity for drugs. In addition to the ADCs, more effective payload strategies using different concepts to achieve the same results are urgently needed. One of the most promising drug carrier is ligand targeted nanoparticle.

Figure 5:
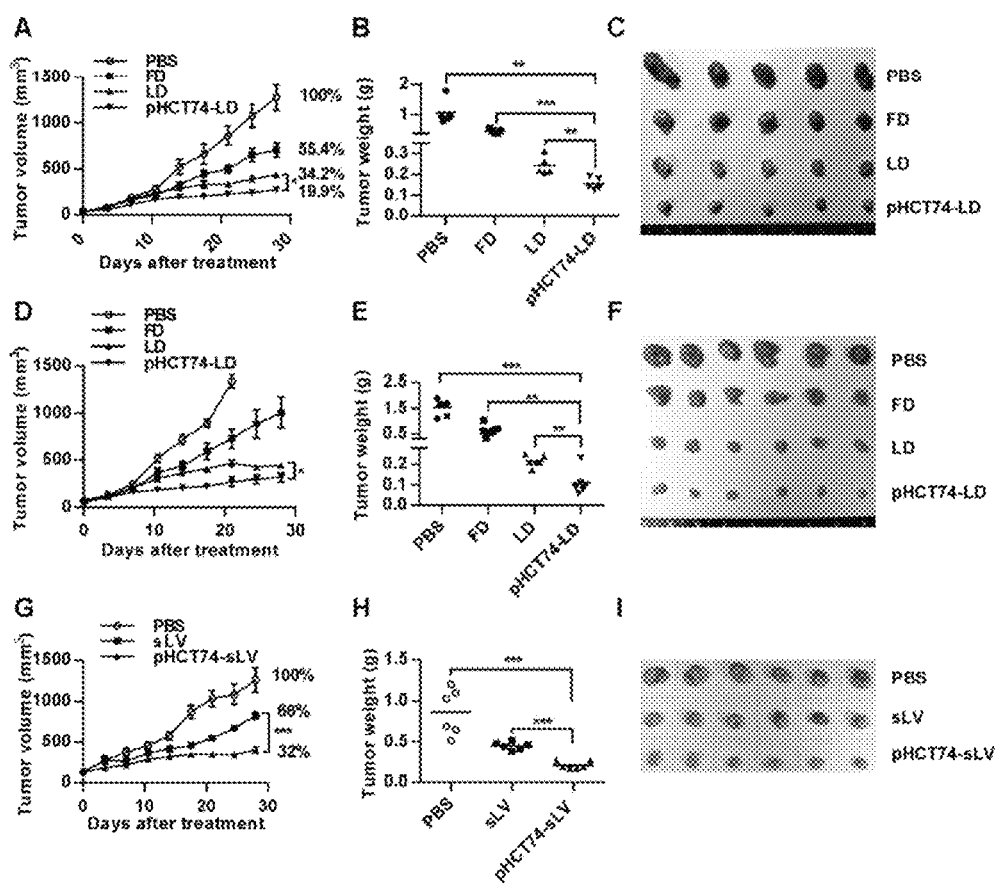
FIG. 5 shows the targeting peptide pHCT74 conjugation enhances efficacy of liposomal doxorubicin and liposomal vinorelbine in colorectal cancer xenograft models. Mice bearing xenografts of human HCT116 (A, B, C) or SW620 (D, E. F) colorectal carcinoma were treated with 1 mg/kg pHCT74-LD, 1 mg/kg LD, 1 mg/kg FD and PBS, respectively. (G, H, I) Antitumor effects of vinorelbine loaded liposome on human colorectal cancer HCT116 xenograft mice. Mice were administered with 1.5 mg/kg pHCT74-sLV, sLV, and PBS, respectively. All compounds were injected twice weekly via tail vein. (C, D; E, F; H, I) At the end of treatment, tumor tissues were dissected and weighed. *, $0.05 \geq P > 0.01$; , $0.01 \geq P > 0.001$; and *, $P < 0.001$. Bars, SEM.
Figure 6:
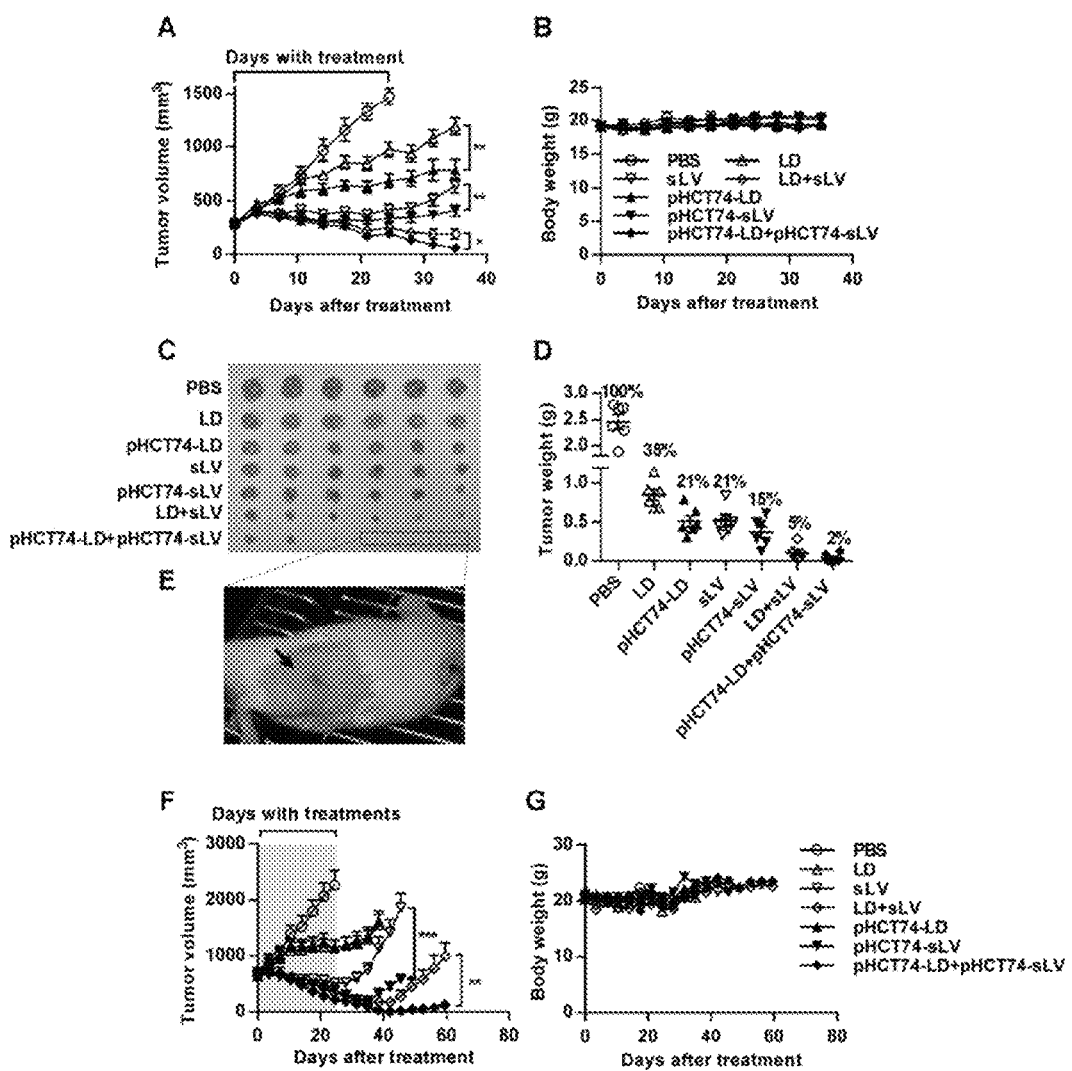
FIG. 6 shows pHCT74 peptide conjugation enhances efficacy of liposomal doxorubicin and liposomal vinorelbine in colorectal cancer xenograft models. Mice bearing HCT116 xenografts (~250 mm$^3$) were randomly separated into 7 treatment groups, with 6 mice per group. Tumor growth (A) and body weight (B) curves for HCT116 xenograft with administration of vehicle (PBS), LD (1 mg/kg), sLV (1.5 mg/kg). LD (1 mg/kg)+sLV (1.5 mg/kg), pHCT74-LD (1 mg/kg), pHCT74-sLV (1.5 mg/kg) or pHCT74-LD (1 mg/kg)+pHCT74-sLV (1.5 mg/kg). At the end of treatment, tumor tissues were dissected. (C) and weighed (D). (E) Three-sixths tumor treated with combinations of 1 mg/kg pHCT74-LD and 1.5 mg/kg pHCT74-LX were eradicated. Mice bearing large HCT116 xenografts (~650 mm$^3$) were treated with vehicle (PBS), LD (1 mg/kg), sLV (2 mg/kg), LD (1 mg/kg)+sLV (2 mg/kg), pHCT74-LD (1 mg/kg), pHCT74-sLV (2 mg/kg) or pHCT74-LD (1 mg/kg)+pHCT74-sLV (2 mg/kg). Tumor growth (F) and body weight (G) curves for the treatments. All compounds were injected twice weekly via tail vein. *, $0.05 \geq P > 0.01$; , $0.01 \geq P > 0.001$; and *, $P < 0.001$. Bars, SEM.
Figure 7:
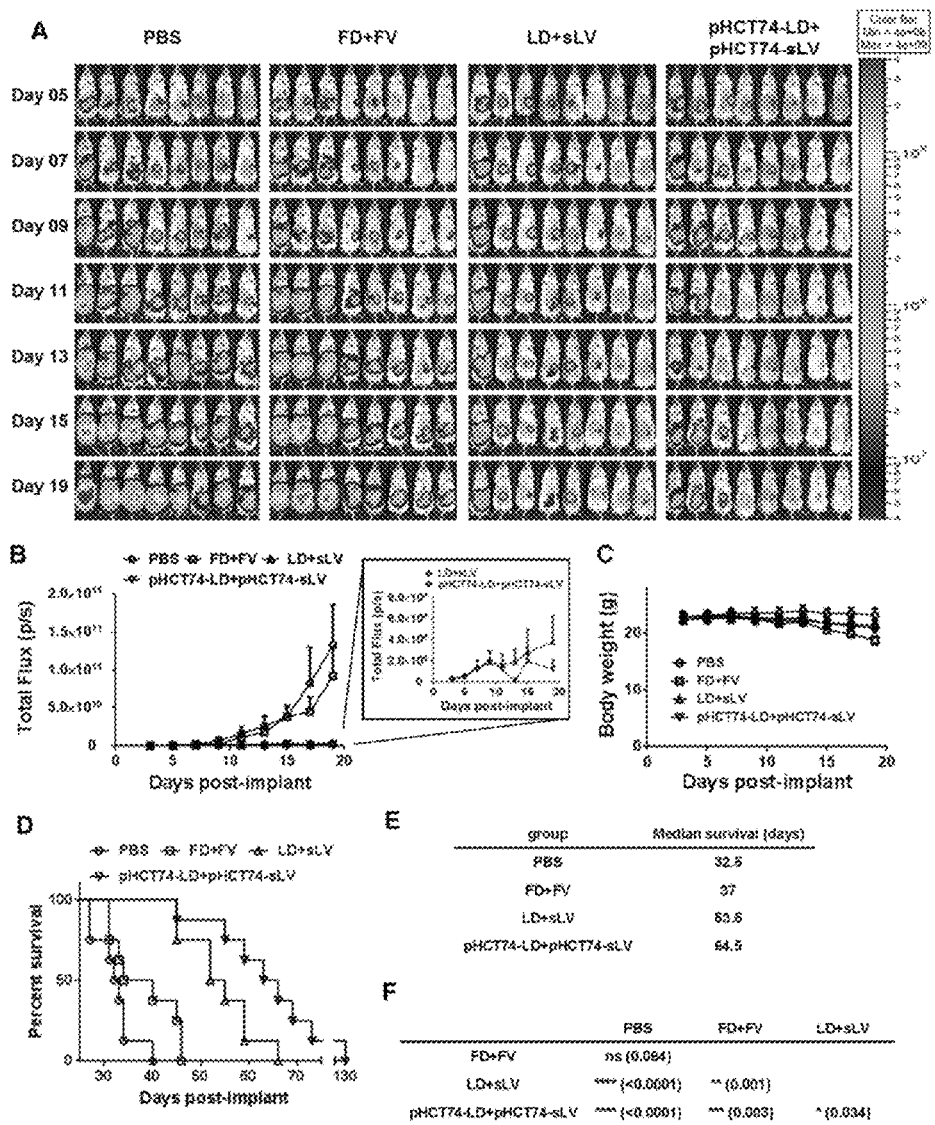
FIG. 7 shows enhanced antitumor effect of combination pHCT74-LD and pHCT74-sLV therapy in an orthotopic colorectal carcinoma model. NSG mice (NOD.Cg-Prkdc$^{scid}$ Il2rg$^{tmIWjl}$/SzJ) were orthotopically implanted with HCT116-luc cells and treated with vehicle (PBS), FD (1 mg/kg)+FV (2 mg/kg), LD (1 mg/kg)+sLV (2 mg/kg) or pHCT74-LD (1 mg/kg)+pHCT74-sLV (2 mg/kg) after 5 days of tumor inoculation. All compounds were injected twice weekly via tail vein. (A) Tumor growth was monitored for bioluminescence using the IVIS 200 Imaging System. (B) Tumor progression monitored by bioluminescence quantification. (C) Body weight. (D) Kaplan-Meier survival plot. (E) median survival of each treatment group. (F) A survival analysis by log-rank (Mantel-Cox) test showing the probability of survival for all subjects. (N=8)

In the present study, we used a lipid based nanoparticle as vehicle to encapsulate chemotherapeutics to achieve high drug loading efficiency. Drug encapsulated in nanoparticles was measured to contain up to 100 g (doxorubicin) or 350 g (vinorelbine) drug/mole phospholipid. We have generated nanoparticles with an average size of 100 nm. Each nanoparticle contained approximately 14,700 doxorubicin or 36,000 vinorelbine molecules. This represents a 3,600- to 18,000-fold capacity improvement over ADCs. Developing ligand-targeted nanoparticles seems to be a logical approach to overcome not only drug loading capacity but also tumor cells specificity, thus resulting in more effective targeted drugs with higher efficacy and lower toxicity (FIGS. 5-7).

We successfully identified alpha-enolase as the target protein of the pHCT74 peptide. Alpha-enolase is a multifunctional protein involved in various processes, such as metabolism, growth control, hypoxia tolerance, extracellular matrix degradation, tumor metastasis and allergic responses. It is a key glycolytic enzyme in the cytoplasm that catalyzes conversion of 2-phosphoglyceric acid to phosphoenolpyruvic acid. Cancer cells are associated with increased rates of glycolysis and glucose transport and increased anaerobic glycolysis in hypoxic conditions known as the Warburg effect. Several reports have shown an upregulation of alpha-enolase at the mRNA and/or protein level in variant types of cancer, including colon cancer, breast cancer, gliomas, lung cancer, leukemia, hepatocellular carcinoma, esophageal cancer, head and neck cancer, pancreatic cancer, prostate cancer, testicular cancer, and ovarian cancer.

In addition to glycolytic enzyme, alpha-enolase is expressed on the cell surface of most tumors, and acts as a plasminogen-binding receptor. It is not known how cytosolic alpha-enolase with no N-terminal signal sequence or transmembrane domain was transported to the plasma membrane and displayed on the cell surface. When alpha-enolase is localized on the cell surface, it forms a multi-protein complex with uPA receptor (uPAR), integrins and certain cytoskeletal proteins that are responsible for adhesion, migration and proliferation. In tumor, it can modulate intravascular and pericellular fibrinolytic activity and promote cell migration and cancer metastasis. Moreover, the expression of alpha-enolase frequently correlates with cancer diagnosis, survival and prognosis. Patients with high alpha-enolase expression are correlated with greater tumor size, poor nodal status and a shorter disease-free interval, and have significantly poorer clinical prognosis than low expressers.

Thus, alpha-enolase could be considered as an ideal therapeutic target for human cancers. Accumulation of evidence revealed that, in addition to its innate glycolytic function, alpha-enolase was associated with multidrug resistance in cancer cells. Alpha-enolase was upregulated in the secretome of the 5-Fluorouracil-resistant cell line. It also showed higher expression in the human breast adenocarcinoma adriamycin-resistant cells when compared with drug-sensitive cells. In addition, a paclitaxel-resistant clonal population of the breast cancer cell line with superinvasive phenotype showed an significant increase in expression levels of alpha-enolase. RNAi-mediated knockdown of alpha-enolase expression in tumor cell lines caused a significant increase in the sensitivity of the cells to anti-tubulin chemotherapeutics (e.g., vincristine and taxol), but not to doxorubicin, etoposide or cisplatinum. It is implied that alpha-enolase was involved in modulating the microtubule network, and the anti-tubulin chemotherapeutics might have the ability to disrupt the alpha-enolase-tubulin interations. Here, the alpha-enolase-targeted lipid nanoparticle that we have developed might have potential to overcome chemotherapy resistance of alpha-enolase overexpressed tumor cells.

The pHCT74-modified liposomal drugs showed a significantly improved therapeutic efficacy in human colorectal carcinoma cells-bearing NOD.CB17-Prkdc$^{scid}$/J mice, and significantly inhibited tumor cell viability, lower tumor volumes and final average tumor weights compared with control non-specific treatments. The rapid and massive accumulation of the pHCT74 targeted liposomes specifically in tumor cells resulted in a prominent tumor growth regression. These therapeutic outcomes confirm the key role of the tumor-specific binding and internalization of the pHCT74-LD and pHCT74-sLV in achieving elevated local concentration of the chemotherapeutic agent inside the tumor. These results indicate that pHCT74-mediated targeting cancer therapy has distinct advantages over conventional chemotherapeutic agents or non-targeted liposomal drugs. Our results should also encourage further research to expand the application of this targeting ligand to various other drug-delivery nanoparticles.

The foregoing description of the exemplary embodiments of the invention has been presented only for the purposes of illustration and description and is not intended to be exhaustive or to limit the invention to the precise forms disclosed. Many modifications and variations are possible in light of the above teaching. Some references, which may include patents, patent applications and various publications, are cited and discussed in the description of this invention. The citation and/or discussion of such references is provided merely to clarity the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A conjugate comprising:
   (a) an isolated or a synthetic targeting peptide of less than 15 amino acid residues in length, comprising an amino acid sequence having at least 90% identity to a sequence selected from the group consisting of SEQ ID NOs: 2 and 3; and
   (b) a component, to which the targeting peptide is conjugated, the component being selected from the group consisting of a drug delivery vehicle, an anti-cancer drug, a micelle, a nanoparticle, liposomes, a polymer, a lipid, an oligonucleotide, a peptide, a polypeptide, a protein, a cell, an imaging agent, and a labeling agent.

2. The conjugate of claim 1, wherein the targeting peptide is conjugated to:
   (a) one or more drugs selected from doxorubicin and vinorelbine; or
   (b) an oligonucleotide; or
   (c) an imaging agent.

3. The conjugate of claim 1, wherein the drug delivery vehicle is selected from the group consisting of liposomes, polymeric micelles, lipoprotein-based drug carriers, nanoparticle drug carriers, dendrimers, stem cells, polypeptides.

4. The conjugate of claim 1, wherein the component is a drug delivery vehicle and the conjugate further comprises at least one anti-cancer drug encapsulated within the drug delivery vehicle.

5. The conjugate of claim 4, wherein the at least one anti-cancer drug is selected from the group consisting of doxorubicin, vinorelbine, and any combination thereof.

6. The conjugate of claim 5, wherein the drug delivery vehicle is a liposome.

7. The conjugate of claim 6, wherein the liposome is PEGylated.

8. The conjugate of claim 1, wherein the targeting peptide comprises an amino acid sequence having at least 95% identity to SEQ ID NO: 3.

9. The conjugate of claim 8, wherein the sequence of the targeting peptide is SEQ ID NO: 3.

10. The conjugate of claim 1, wherein the component is a labeling agent, to which the C-terminus of the targeting peptide is conjugated.

11. The conjugate of claim 10, further comprising:
    (a) a cancer cell, bound to the targeting peptide; and
    (b) a cross-linker, cross-linking the cancer cell to the targeting peptide.

12. The conjugate of claim 1, wherein the component is alpha-enolase.

13. A composition comprising:
    (a) a therapeutically effective amount of the conjugate of claim 4; and
    (b) a pharmaceutically acceptable excipient, carrier or vehicle.

14. A composition comprising:
(a) a therapeutically effective amount of the conjugate of claim 6, wherein the anti-cancer drug is doxorubicin;
(b) a therapeutically effective amount of the conjugate of claim 6, wherein the anti-cancer drug is vinorelbine; and
(c) a pharmaceutically acceptable excipient, carrier or vehicle.

15. A method of treating cancer cells, comprising:
administering to a subject having the cancer cells the composition of claim 14.

16. The method of claim 15, wherein the targeting peptide is SEQ ID NO: 3.

17. The method of claim 15, wherein the cancer cells comprise alpha-enolase on the surface thereof.

* * * * *

SEQUENCE LISTING

```
<160> NUMBER OF SEQ ID NOS: 23

<210> SEQ ID NO 1
<211> LENGTH: 12
<212> TYPE: PRT
<213> ORGANISM: Artificial Sequence
<220> FEATURE:
<223> OTHER INFORMATION: HCT-63

<400> SEQUENCE: 1

Arg Leu Asn Leu Asp Ile Ile Ala Val Thr Ser Val
1               5                   10

<210> SEQ ID NO 2
<211> LENGTH: 12
<212> TYPE: PRT
<213> ORGANISM: Artificial Sequence
<220> FEATURE:
<223> OTHER INFORMATION: HCT-69
```

```
<400> SEQUENCE: 2

Thr Ser Val Ser Ile Val Ser Thr Val Leu Thr Pro
1               5                   10

<210> SEQ ID NO 3
<211> LENGTH: 12
<212> TYPE: PRT
<213> ORGANISM: Artificial Sequence
<220> FEATURE:
<223> OTHER INFORMATION: HCT-74

<400> SEQUENCE: 3

Ser Ser Met Asp Ile Val Leu Arg Ala Pro Leu Met
1               5                   10

<210> SEQ ID NO 4
<211> LENGTH: 12
<212> TYPE: PRT
<213> ORGANISM: Artificial Sequence
<220> FEATURE:
<223> OTHER INFORMATION: HCT-01

<400> SEQUENCE: 4

Ala Ala Pro Glu Leu Val Ala Pro Ser Ile Trp Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: HCT-40

<400> SEQUENCE: 5

Ser Leu Ser Leu Val Ala Pro Val Leu Ser Leu Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: HCT-70

<400> SEQUENCE: 6

Thr Met Gly Phe Thr Ala Pro Arg Phe Pro His Tyr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: HCT-50

<400> SEQUENCE: 7

Ser Pro Gly Leu Ser Leu Val Ser His Met Gln Thr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: HCT-41
```

```
<400> SEQUENCE: 8

Leu Thr Arg Pro Asn Gly Ile Pro His Leu Ser Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: HCT-21

<400> SEQUENCE: 9

Thr Ser Tyr Ser Ile Asn Leu Leu Ser Thr Pro Met
1               5                   10

<210> SEQ ID NO 10
<211> LENGTH: 12
<212> TYPE: PRT
<213> ORGANISM: Artificial Sequence
<220> FEATURE:
<223> OTHER INFORMATION: HCT-10

<400> SEQUENCE: 10

Ser Pro Thr Gly Leu Phe Met Thr Leu Ser Ser Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: HCT-04

<400> SEQUENCE: 11

His His Arg Thr Leu Ser Pro Ser Val Ser Ile Leu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: HCT-08

<400> SEQUENCE: 12

Leu Ala Thr Pro Phe Thr Ala Thr Ser Ala Thr Gly
1               5                   10

<210> SEQ ID NO 13
<211> LENGTH: 12
<212> TYPE: PRT
<213> ORGANISM: Artificial Sequence
<220> FEATURE:
<223> OTHER INFORMATION: HCT-71

<400> SEQUENCE: 13

Val Thr Ser Ser Leu Pro Arg Met Phe His Thr Leu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: HCT-12

<400> SEQUENCE: 14
```

```
Gly Phe Leu Pro Leu Pro Arg Gly Glu Ile Phe Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: HCT-92

<400> SEQUENCE: 15

Thr Pro Ser Leu Pro Pro Thr Met Phe Arg Leu Thr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: HCT-59

<400> SEQUENCE: 16

Gly His Leu Ile Pro Leu Arg Gln Pro Ser His Gln
1               5                   10

<210> SEQ ID NO 17
<211> LENGTH: 12
<212> TYPE: PRT
<213> ORGANISM: Artificial Sequence
<220> FEATURE:
<223> OTHER INFORMATION: HCT-47

<400> SEQUENCE: 17

Ser Pro Asn Phe Ser Trp Leu Pro Leu Gly Thr Thr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: HCT-33

<400> SEQUENCE: 18

Val Asp Ala Gly Leu Gly Ser Ile Phe Leu Leu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: HCT-34

<400> SEQUENCE: 19

Trp Gly Ile Thr Val Glu Thr Ala Tyr Gly Thr Ala
1               5                   10

<210> SEQ ID NO 20
<211> LENGTH: 12
<212> TYPE: PRT
<213> ORGANISM: Artificial Sequence
<220> FEATURE:
<223> OTHER INFORMATION: HCT-35

<400> SEQUENCE: 20
```

Ser Glu Leu His Val Arg Leu Ser His Ile Asn Ala
1               5                   10

<210> SEQ ID NO 21
<211> LENGTH: 12
<212> TYPE: PRT
<213> ORGANISM: Artificial Sequence
<220> FEATURE:
<223> OTHER INFORMATION: HCT-45

<400> SEQUENCE: 21

Ser Ser Gly Gly Val Arg Trp Ser Ala His Trp Ser
1               5                   10

<210> SEQ ID NO 22
<211> LENGTH: 434
<212> TYPE: PRT
<213> ORGANISM: Homo sapiens

<400> SEQUENCE: 22

Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Asn Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Gly Leu
    210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Lys Asp Tyr Pro
        275                 280                 285

Val Val Ser Ile Glu Asp Pro Phe Asp Gln Asp Asp Trp Gly Ala Trp

```
                        290                 295                 300
Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                325                 330                 335

Cys Asn Cys Leu Leu Leu Lys Val Asn Gln Ile Gly Ser Val Thr Glu
                340                 345                 350

Ser Leu Gln Ala Cys Lys Leu Ala Gln Ala Asn Gly Trp Gly Val Met
            355                 360                 365

Val Ser His Arg Ser Gly Glu Thr Glu Asp Thr Phe Ile Ala Asp Leu
        370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                405                 410                 415

Leu Gly Ser Lys Ala Lys Phe Ala Gly Arg Asn Phe Arg Asn Pro Leu
                420                 425                 430

Ala Lys

<210> SEQ ID NO 23
<211> LENGTH: 20
<212> TYPE: PRT
<213> ORGANISM: Artificial Sequence
<220> FEATURE:
<223> OTHER INFORMATION: -96 gIII sequencing primer

<400> SEQUENCE: 23

Cys Cys Cys Thr Cys Ala Thr Ala Gly Thr Thr Ala Gly Cys Gly Thr
1               5                   10                  15

Ala Ala Cys Gly
            20
```